(12) United States Patent
Terliuc et al.

(10) Patent No.: US 10,610,086 B2
(45) Date of Patent: Apr. 7, 2020

(54) BALLOON ENDOSCOPE AND METHODS OF MANUFACTURE AND USE THEREOF

(71) Applicant: SMART Medical Systems Ltd., Ra'anana (IL)

(72) Inventors: Gad Terliuc, Ra'anana (IL); Gilad Luria, Givataim (IL)

(73) Assignee: SMART Medical Systems Ltd., Ra'anana (IL)

( * ) Notice: Subject to any disclaimer, the term of this patent is extended or adjusted under 35 U.S.C. 154(b) by 0 days.

(21) Appl. No.: 16/048,031

(22) Filed: Jul. 27, 2018

(65) Prior Publication Data

US 2018/0333043 A1    Nov. 22, 2018

Related U.S. Application Data

(62) Division of application No. 13/583,634, filed as application No. PCT/IL2011/000222 on Mar. 9, 2011, now Pat. No. 10,052,014.

(Continued)

(51) Int. Cl.
*A61B 1/015* (2006.01)
*A61B 1/00* (2006.01)
(Continued)

(52) U.S. Cl.
CPC ............ *A61B 1/015* (2013.01); *A61B 1/0011* (2013.01); *A61B 1/00057* (2013.01);
(Continued)

(58) Field of Classification Search
CPC . A61B 1/015; A61B 1/00057; A61B 1/00082; A61B 1/0011; A61B 1/31
(Continued)

(56) References Cited

U.S. PATENT DOCUMENTS 3,837,347 A    9/1974    Tower
3,884,242 A *  5/1975    Bazell ................... A61M 16/04
                                                128/207.14
(Continued)

FOREIGN PATENT DOCUMENTS

CA    2661242    10/2010
CN    1394543    2/2003
(Continued)

OTHER PUBLICATIONS

Single Balloon Endoscope: Balloon pump control OBCU: http :-- medical. olympusamerica. com-products- control-ballooncontrol- unitobcu, [online].
(Continued)

*Primary Examiner* — Timothy J Neal
*Assistant Examiner* — Jae Woo
(74) *Attorney, Agent, or Firm* — Knobbe, Martens, Olson & Bear, LLP

(57) ABSTRACT

A balloon endoscope including an endoscope body having a selectably pressurizable interior volume, which generally fills the interior of the endoscope body and a selectably inflatable balloon located on an outer surface of the endoscope body and defining a balloon volume which communicates with the interior volume for selectable inflation of the balloon by selectable pressurization of the interior volume.

10 Claims, 26 Drawing Sheets

Related U.S. Application Data

(60) Provisional application No. 61/457,236, filed on Feb. 9, 2011, provisional application No. 61/344,690, filed on Sep. 14, 2010, provisional application No. 61/282,623, filed on Mar. 9, 2010, provisional application No. 61/282,624, filed on Mar. 9, 2010.

(51) Int. Cl.
    *A61B 1/31*     (2006.01)
    *A61B 1/32*     (2006.01)
    *A61B 90/00*     (2016.01)

(52) U.S. Cl.
CPC ............ *A61B 1/00082* (2013.01); *A61B 1/31* (2013.01); *A61B 1/32* (2013.01); *A61B 2090/0809* (2016.02); *Y10T 29/49817* (2015.01); *Y10T 29/49826* (2015.01)

(58) Field of Classification Search
USPC ................................ 600/115, 116, 153, 159; 604/97.01–97.03, 98.01, 99.01, 604/102.01–102.03
See application file for complete search history.

(56) References Cited

U.S. PATENT DOCUMENTS

| | | |
|---|---|---|
| 3,895,637 A | 7/1975 | Choy |
| 4,040,413 A | 8/1977 | Ohshiro |
| 4,148,307 A | 4/1979 | Utsugi |
| 4,176,662 A | 12/1979 | Frazer |
| 4,195,637 A | 4/1980 | Gruntzig et al. |
| 4,224,929 A * | 9/1980 | Furihata .............. A61B 1/00082 600/107 |
| 4,261,339 A | 4/1981 | Hanson et al. |
| 4,351,341 A * | 9/1982 | Goldberg ......... A61B 17/22032 600/587 |
| 4,444,188 A * | 4/1984 | Bazell .............. A61B 17/22032 604/103 |
| 4,453,545 A | 6/1984 | Inoue |
| 4,616,652 A | 10/1986 | Simpson |
| 4,676,228 A | 6/1987 | Krasner et al. |
| 4,681,093 A * | 7/1987 | Ono .................... A61B 1/00082 600/116 |
| 4,690,131 A | 9/1987 | Lyddy et al. |
| 4,721,123 A | 1/1988 | Cosentino et al. |
| 4,862,874 A | 9/1989 | Kellner |
| 4,917,088 A | 4/1990 | Crittenden |
| 5,135,487 A | 8/1992 | Morrill et al. |
| 5,259,366 A | 11/1993 | Reydel et al. |
| 5,310,524 A | 5/1994 | Campbell et al. |
| 5,338,299 A * | 8/1994 | Barlow ............... A61M 25/104 604/103 |
| 5,411,016 A * | 5/1995 | Kume ................ A61B 1/00082 600/114 |
| 5,445,646 A * | 8/1995 | Euteneuer ................. A61F 2/95 604/103.02 |
| 5,454,364 A | 10/1995 | Kruger |
| 5,569,220 A | 10/1996 | Webster, Jr. |
| 5,593,419 A | 1/1997 | Segar |
| 5,599,301 A | 2/1997 | Jacobs et al. |
| 5,607,441 A | 3/1997 | Sierocuk et al. |
| 5,653,240 A | 8/1997 | Zimmon |
| 5,693,014 A | 12/1997 | Abele et al. |
| 5,700,242 A | 12/1997 | Mulder |
| 5,707,382 A * | 1/1998 | Sierocuk ............ A61B 17/0218 600/207 |
| 5,707,392 A | 1/1998 | Kortenbach |
| 5,803,901 A * | 9/1998 | Chin ................. A61B 17/0218 600/190 |
| 5,823,940 A | 10/1998 | Newman |
| 5,851,477 A * | 12/1998 | Halgren ............. A61M 25/0009 264/512 |
| 5,904,701 A | 5/1999 | Daneshvar |
| 5,984,860 A | 11/1999 | Shan |
| 6,007,482 A | 12/1999 | Madni et al. |
| 6,162,171 A | 12/2000 | Ng et al. |
| 6,261,260 B1 | 7/2001 | Maki et al. |
| 6,412,334 B1 * | 7/2002 | Kral .................... A61B 1/00057 73/40 |
| 6,461,294 B1 | 10/2002 | Oneda et al. |
| 6,485,684 B1 * | 11/2002 | Mapson .............. A61B 1/00057 206/210 |
| 6,585,639 B1 * | 7/2003 | Kotmel ............... A61B 1/00082 600/114 |
| 6,589,208 B2 | 7/2003 | Ewers et al. |
| 6,663,589 B1 | 12/2003 | Halevy |
| 6,695,810 B2 | 2/2004 | Peacock, III et al. |
| 6,702,735 B2 | 3/2004 | Kelly |
| 6,764,441 B2 | 7/2004 | Chiel et al. |
| 6,986,736 B2 * | 1/2006 | Williams ........... A61B 1/00057 600/101 |
| 7,081,096 B2 * | 7/2006 | Brister ............... A61B 1/00082 600/549 |
| 7,169,140 B1 * | 1/2007 | Kume ................. A61B 1/00082 604/529 |
| 7,635,346 B2 | 12/2009 | Cabiri et al. |
| 7,695,428 B2 | 4/2010 | Machida |
| 7,699,771 B2 | 4/2010 | Wendlandt |
| 7,713,191 B2 * | 5/2010 | Sekiguchi .......... A61B 1/00055 600/115 |
| 7,837,672 B2 | 11/2010 | Intoccia |
| 7,887,480 B2 | 2/2011 | Sekiguchi |
| 7,918,788 B2 | 4/2011 | Lin et al. |
| 7,963,911 B2 | 6/2011 | Terliuc |
| 8,002,698 B2 | 8/2011 | Motai et al. |
| 8,012,084 B2 * | 9/2011 | Machida ............ A61B 1/00082 600/114 |
| 8,152,715 B2 * | 4/2012 | Root ................... A61B 1/00034 600/131 |
| 8,187,221 B2 | 5/2012 | Bates |
| 8,197,463 B2 | 6/2012 | Intoccia |
| 8,273,013 B2 | 9/2012 | Niwa et al. |
| 8,419,678 B2 | 4/2013 | Cabiri et al. |
| 8,480,572 B2 | 7/2013 | Takakazu |
| 8,545,382 B2 | 10/2013 | Suzuki et al. |
| 8,727,970 B2 | 5/2014 | Terliuc et al. |
| 8,939,895 B2 | 1/2015 | Simchony et al. |
| 9,119,532 B2 | 9/2015 | Terliuc et al. |
| 9,427,142 B2 | 8/2016 | Terliuc et al. |
| 9,480,390 B2 | 11/2016 | Farhadi |
| 9,521,945 B2 | 12/2016 | Farhadi |
| 9,596,979 B2 | 3/2017 | Terliuc et al. |
| 9,661,994 B2 | 5/2017 | Terliuc et al. |
| 10,052,014 B2 | 8/2018 | Terliuc et al. |
| 2001/0032494 A1 * | 10/2001 | Greszler ............ A61B 1/00057 73/40 |
| 2002/0147385 A1 * | 10/2002 | Butler ................ A61B 1/00154 600/114 |
| 2003/0074015 A1 | 4/2003 | Nakao |
| 2003/0236495 A1 * | 12/2003 | Kennedy, II .......... A61M 25/10 604/97.02 |
| 2004/0102681 A1 | 5/2004 | Gross |
| 2004/0210116 A1 | 10/2004 | Nakao |
| 2004/0236366 A1 * | 11/2004 | Kennedy, II .......... A61M 25/10 606/192 |
| 2005/0027253 A1 | 2/2005 | Castellano et al. |
| 2005/0124856 A1 | 6/2005 | Fuji Kura Tetsuya et al. |
| 2005/0125005 A1 | 6/2005 | Fujikura |
| 2005/0133453 A1 | 6/2005 | Woodruff et al. |
| 2005/0137457 A1 | 6/2005 | Machida |
| 2005/0159702 A1 | 7/2005 | Sekiguchi et al. |
| 2005/0165233 A1 | 7/2005 | Hamedi et al. |
| 2005/0165273 A1 | 7/2005 | Takano |
| 2005/0171400 A1 | 8/2005 | Itoi |
| 2005/0197668 A1 * | 9/2005 | Lim .................. A61M 25/1002 606/194 |
| 2006/0095063 A1 | 5/2006 | Sekiauchi |
| 2006/0100480 A1 | 5/2006 | Ewers et al. |
| 2006/0111610 A1 | 5/2006 | Machida |
| 2006/0116549 A1 | 6/2006 | Sekiguchi et al. |
| 2006/0161044 A1 | 7/2006 | Oneda et al. |

(56) References Cited

U.S. PATENT DOCUMENTS

| | | | |
|---|---|---|---|
| 2006/0167538 A1* | 7/2006 | Rucker | A61F 2/04 623/1.25 |
| 2006/0282088 A1 | 12/2006 | Ryan | |
| 2007/0010785 A1 | 1/2007 | Sekiguchi et al. | |
| 2007/0038026 A1* | 2/2007 | Yoshida | A61B 1/00082 600/116 |
| 2007/0083158 A1 | 4/2007 | Hirszowicz et al. | |
| 2007/0100280 A1* | 5/2007 | van Sloten | A61M 25/0009 604/103.1 |
| 2007/0185385 A1 | 8/2007 | Noguchi et al. | |
| 2007/0191678 A1 | 8/2007 | Sekiguchi | |
| 2007/0213586 A1 | 9/2007 | Kenji et al. | |
| 2007/0244361 A1 | 10/2007 | Ikeda et al. | |
| 2007/0270645 A1 | 11/2007 | Ikeda | |
| 2007/0276181 A1* | 11/2007 | Terliuc | A61B 1/00082 600/106 |
| 2008/0009673 A1 | 1/2008 | Khachi | |
| 2008/0161645 A1 | 7/2008 | Goldwasser et al. | |
| 2008/0177142 A1 | 7/2008 | Roskopf | |
| 2008/0200759 A1 | 8/2008 | Niwa et al. | |
| 2008/0306441 A1* | 12/2008 | Brown | A61M 25/10 604/99.01 |
| 2009/0012469 A1 | 1/2009 | Nita | |
| 2009/0018500 A1* | 1/2009 | Carter | A61M 25/10 604/99.01 |
| 2009/0048483 A1 | 2/2009 | Yamamoto | |
| 2009/0156896 A1 | 6/2009 | Kura | |
| 2009/0187069 A1 | 7/2009 | Terliuc et al. | |
| 2009/0234188 A1 | 9/2009 | Matsuura et al. | |
| 2009/0287058 A1 | 11/2009 | Terliuc | |
| 2010/0041951 A1 | 2/2010 | Glozman et al. | |
| 2010/0042046 A1 | 2/2010 | Chang et al. | |
| 2010/0217185 A1 | 8/2010 | Terliuc et al. | |
| 2012/0178994 A1 | 7/2012 | Schembre | |
| 2012/0232342 A1 | 9/2012 | Reydel | |
| 2012/0285488 A1 | 11/2012 | Labib et al. | |
| 2013/0023920 A1 | 1/2013 | Terliuc et al. | |
| 2013/0090527 A1 | 4/2013 | Axon | |
| 2013/0116549 A1 | 5/2013 | Gunday et al. | |
| 2014/0088362 A1 | 3/2014 | Terliuc et al. | |
| 2015/0335229 A1 | 11/2015 | Terliuc | |
| 2016/0022120 A1 | 1/2016 | Terliuc et al. | |
| 2016/0081536 A1 | 3/2016 | Farhad | |
| 2017/0027415 A1 | 2/2017 | Terliuc et al. | |
| 2017/0027433 A1 | 2/2017 | Terliuc | |
| 2017/0065155 A1 | 3/2017 | Farhadi | |
| 2017/0100017 A1 | 4/2017 | Terliuc et al. | |
| 2017/0203080 A1 | 7/2017 | Terliuc et al. | |
| 2017/0360282 A1 | 12/2017 | Terliuc et al. | |
| 2018/0333043 A1 | 11/2018 | Terliuc et al. | |

FOREIGN PATENT DOCUMENTS

| | | |
|---|---|---|
| CN | 2624936 | 7/2004 |
| CN | 1550203 | 12/2004 |
| CN | 1636502 | 7/2005 |
| CN | 1647747 | 8/2005 |
| CN | 1649630 | 8/2005 |
| CN | 1827031 | 9/2006 |
| CN | 1917802 | 2/2007 |
| CN | 1933766 | 3/2007 |
| CN | 1946328 | 4/2007 |
| CN | 1951312 | 4/2007 |
| CN | 1964665 | 5/2007 |
| CN | 101015440 | 8/2007 |
| CN | 101103898 | 1/2008 |
| CN | 101347321 | 1/2008 |
| CN | 101243965 | 8/2008 |
| CN | 101380220 | 3/2009 |
| CN | 101396256 | 4/2009 |
| CN | 101522091 | 9/2009 |
| CN | 101541227 | 9/2009 |
| CN | 101664560 | 3/2010 |
| CN | 102791180 | 11/2012 |
| CN | 103269638 | 8/2013 |
| DE | 4317601 | 12/1994 |
| DE | 10209993 | 4/2003 |
| EP | 0473045 A1 | 3/1992 |
| EP | 0733342 | 9/1996 |
| EP | 1335659 | 8/2003 |
| EP | 1433410 | 6/2004 |
| EP | 1547641 | 6/2005 |
| EP | 1550465 A1 | 7/2005 |
| EP | 1551316 | 7/2005 |
| EP | 1656879 | 5/2006 |
| EP | 1666864 A1 | 6/2006 |
| EP | 1706169 | 10/2006 |
| EP | 1707221 A1 | 10/2006 |
| EP | 0212696 | 4/2007 |
| EP | 1556118 | 7/2007 |
| EP | 1726248 | 6/2008 |
| EP | 2108303 A1 | 10/2009 |
| EP | 2110068 | 10/2009 |
| EP | 2320984 | 5/2011 |
| EP | 2764818 A1 | 8/2014 |
| JP | S48-068542 | 6/1973 |
| JP | S57-57804 | 4/1982 |
| JP | S62-002925 | 6/1985 |
| JP | SH06I-284226 | 12/1986 |
| JP | SH062-002925 | 1/1987 |
| JP | S61-202274 | 7/1988 |
| JP | SH063-I02429 | 7/1988 |
| JP | SH064-017203 | 1/1989 |
| JP | H2-58402 | 4/1990 |
| JP | H04-102436 | 4/1992 |
| JP | H04-297219 | 10/1992 |
| JP | HEI05337081 | 12/1993 |
| JP | H06-63045 | 3/1994 |
| JP | HEI6-339455 | 12/1994 |
| JP | HEI7-12101 | 2/1995 |
| JP | HEI7-148105 | 6/1995 |
| JP | H08228996 | 9/1996 |
| JP | HEI10-127571 | 5/1998 |
| JP | HEI10-286309 | 10/1998 |
| JP | HEI11-225947 | 8/1999 |
| JP | 2000-060793 | 2/2000 |
| JP | 2000-329534 | 11/2000 |
| JP | 2002-34900 | 2/2002 |
| JP | 2002-301019 | 10/2002 |
| JP | 2003-250896 | 9/2003 |
| JP | 2003-275173 | 9/2003 |
| JP | 2004-97718 | 4/2004 |
| JP | 2004-329720 | 11/2004 |
| JP | 2005-185704 | 7/2005 |
| JP | 2005-185706 | 7/2005 |
| JP | 2005-185707 | 7/2005 |
| JP | 2005-279128 | 10/2005 |
| JP | 2005-296256 | 10/2005 |
| JP | 2005-334475 | 12/2005 |
| JP | 2006-130014 | 5/2006 |
| JP | 2006-167310 | 5/2006 |
| JP | 2006-304906 | 11/2006 |
| JP | 2006-334149 | 12/2006 |
| JP | 2007-014475 | 1/2007 |
| JP | 2007-026814 | 2/2007 |
| JP | 2007-130082 | 5/2007 |
| JP | 2007-517576 | 7/2007 |
| JP | 2007-521907 | 8/2007 |
| JP | 2007-268137 | 10/2007 |
| JP | 2007-268147 | 10/2007 |
| JP | 2007-296054 | 10/2007 |
| JP | 2008-006000 | 1/2008 |
| JP | 2008125886 | 6/2008 |
| JP | 2008-537493 | 9/2008 |
| JP | 2009-056121 | 3/2009 |
| JP | 2009-195321 | 9/2009 |
| JP | 2009-537212 | 10/2009 |
| JP | 2009-254554 | 11/2009 |
| JP | 2012-504431 | 4/2010 |
| SH | 050-016762 | 2/1975 |
| WO | WO 96/00099 | 1/1996 |
| WO | WO 98/30249 | 7/1998 |
| WO | WO 02/094087 | 11/2002 |

(56) References Cited

FOREIGN PATENT DOCUMENTS

| | | |
|---|---|---|
| WO | WO 2005/017854 | 2/2005 |
| WO | WO 2005/074377 | 8/2005 |
| WO | WO 2005/089625 | 9/2005 |
| WO | WO 2006/123590 | 11/2006 |
| WO | WO 2006123590 | 11/2006 |
| WO | WO 2007/023492 | 3/2007 |
| WO | WO 2007/135665 | 11/2007 |
| WO | WO 2008/004228 | 1/2008 |
| WO | WO 2008073126 | 6/2008 |
| WO | WO 2008121143 | 10/2008 |
| WO | WO 2008/142685 | 11/2008 |
| WO | WO 2009/122395 | 10/2009 |
| WO | WO 2010/046891 | 4/2010 |
| WO | WO 2010070291 | 6/2010 |
| WO | WO 2010/137025 | 12/2010 |
| WO | WO 2011/111040 | 9/2011 |
| WO | WO 2014/188402 | 11/2014 |

OTHER PUBLICATIONS

EVIS EXERA II CL V-I 80 product brochure, http:--www.olympus.nl-medical- en-medical_systems-hidden- downloadJ sp. jsp?link=-medical-rmt-media-content-content I-documents I-brochures // EVIS EXERA_11_CL V-I 80 product_brochure_00 I_VI-en_GB_20000 I 0 I. pdf,[online].

BS-2 Front Balloon, http:--www.fujifilmusa.com-products-medical-endoscopy-endoscopes-specializedballoons-andovertube-index. html#balloonsspecifications, [online].

An International Search Report and a Written Opinion both dated Oct. 18, 2011, which issued during the prosecution of Applicant's PCT-IL201 I-000222.

An International Preliminary Report on Patentability dated Sep. 11, 2012, which issued during the prosecution of Applicant's PCT-IL201 I-000222.

BS-2 Front Balloon, http:--www.fujifilmusa.com-products-medical-endoscopy-endoscopes-specialized-balloons-and- overtube-index.html#balloonsspecification, [online], [retrieved on Jun. 3, 2015].

Double Balloon Endoscope: EC-450B 15 colonoscope: http:--www.fujifilmusa.com-products-medical-endoscopy-en do scopes- entero scopes-index. html, [online].

Double Balloon Endoscope: Balloon pump controller BP-30: http:--www.fujifilmusa.com-products-medical-endoscopy-endoscopes-balloon-pump-controller-index. html, [online].

Double Balloon Endoscope: EPX-4440HD video system: http:--www.fujifilmusa.com-products-medical-endoscopy-video-systems- epx-4440hd, [online].

Double Balloon Endoscope: TS-13 101 overtube: http:--www.fujifilmusa.com-products-medical-endoscopy-endoscopes-specialized-balloons-and-overtube-index.html, [online].

Double Balloon Endoscope: EC-450B15 colonoscope: http:--www.fujifilmusa.com-products-medical-endoscopy-1 endoscopes-enteroscopes-index.html,[online],[retrieved on May 10, 2015].

Double Balloon Endoscope: Balloon pump controller BP-20: http:--www.fujifilmusa.com-products-medical-endoscopy- endoscopes-balloon-pump-controller-index. html, [online],[retrieved on May 10, 2015].

Double Balloon Endoscope: EPX-4400HD video system: http:--www.fujifilmusa.com-products-medical-endoscopy- video-systems-epx-4440hd,[online],[retrieved on May 10, 2015].

Double Balloon Endoscope: TS-13 101 overtube: http:--www.fujifilmusa.com-products-medical-endoscopy-endoscopes- specialized-balloons-and-overtube-index.html,[online],[retrieved on May 10, 2015].

EVIS EXERA II CLV-180 product brochure, http:--www.olympus.nl-medical-en-medical_systems-hidden-download_jsp.jsp?link=-medical-rmt-media-content-content_1-documents_1-brochures_1-EVIS_EXERA_II_CLV-180_product_brochure_001_V1-en_GB_20000101.pdf, [online], [retrieved on Jun. 3, 2015].

Single Balloon Endoscope: Balloon pump control OBCU: http:--medical.olympusamerica.com-products-control-balloon- control-unit-obcu,[online], [retrieved on May 10, 2015].

Single Balloon Endoscope: SIF-Q 1 80 enteroscope: http:--medical.olympusamerica.com-products-enteroscope-evis- exera-ii-sif-q180,[online],[retrieved on May 10, 2015].

Single Balloon Endoscope: ST- SB 1 overtube: http:--medical.olympusamerica.com-products-tubes-single-use-st-sb1 1, [online],[retrieved on May 10, 2015].

Single Balloon Endoscope: SIF-Q 1 80 enteroscope: http:--medical.olympusamerica.com-products-enteroscope-evisexera-ii-sifq180, [online].

\* cited by examiner

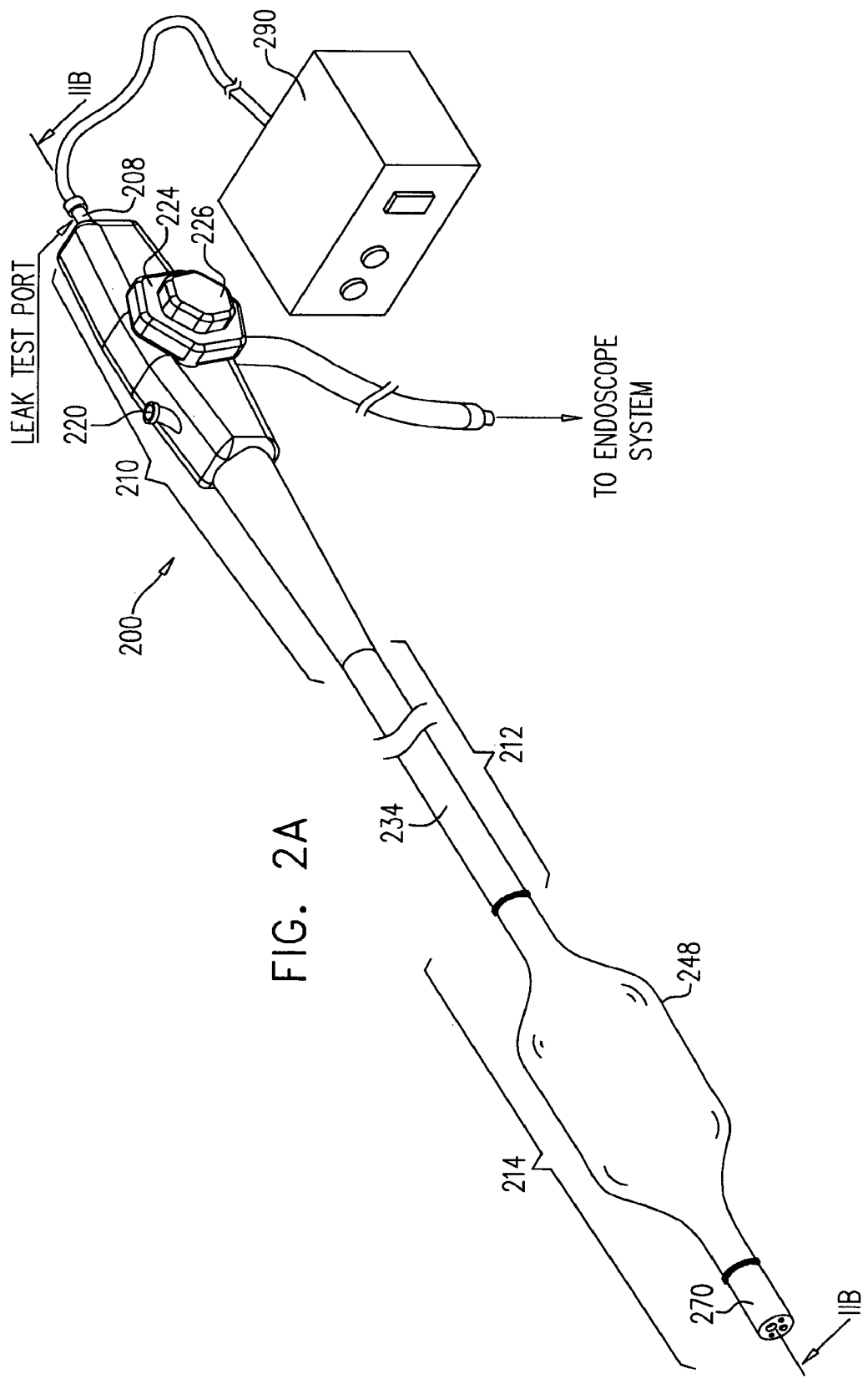

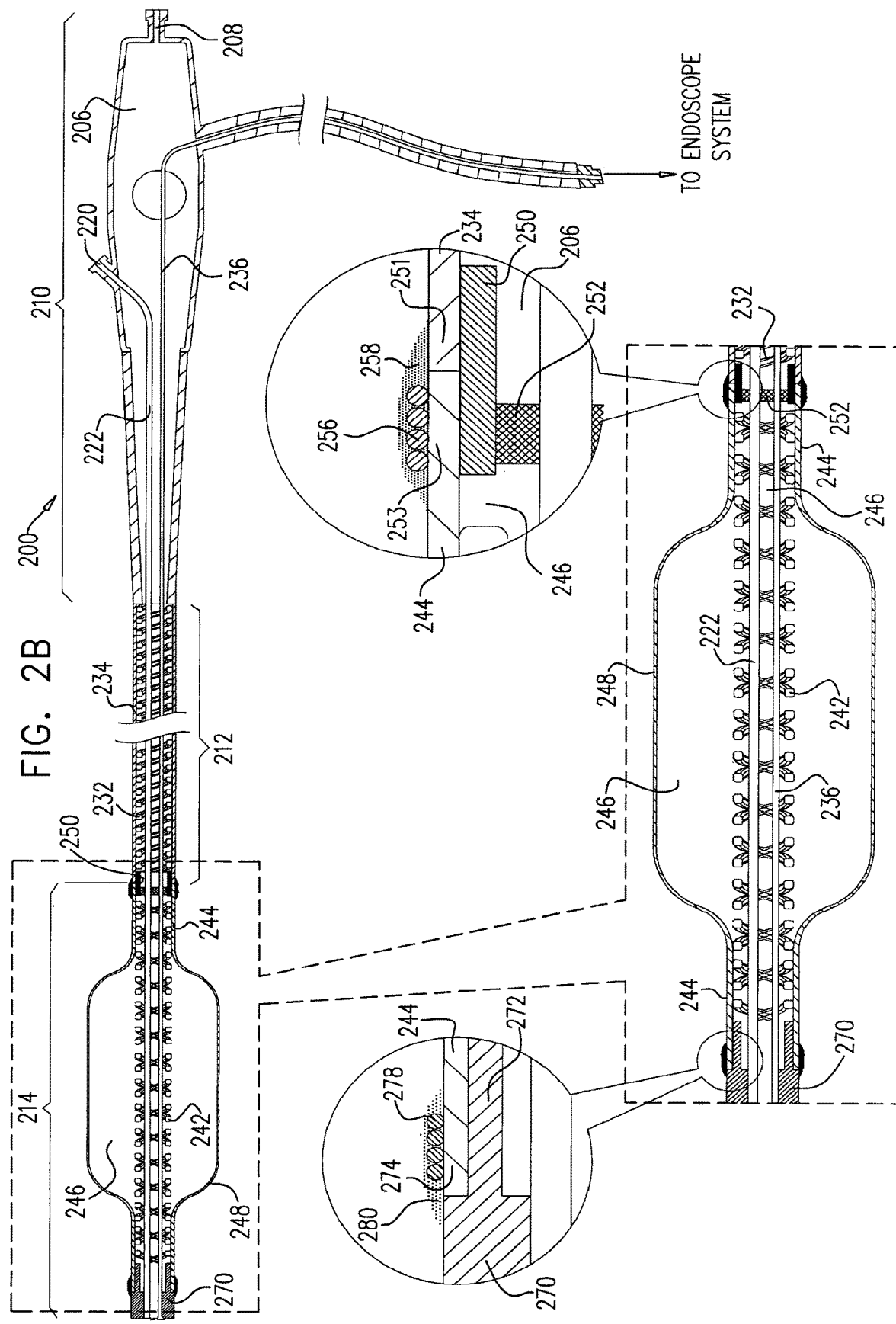

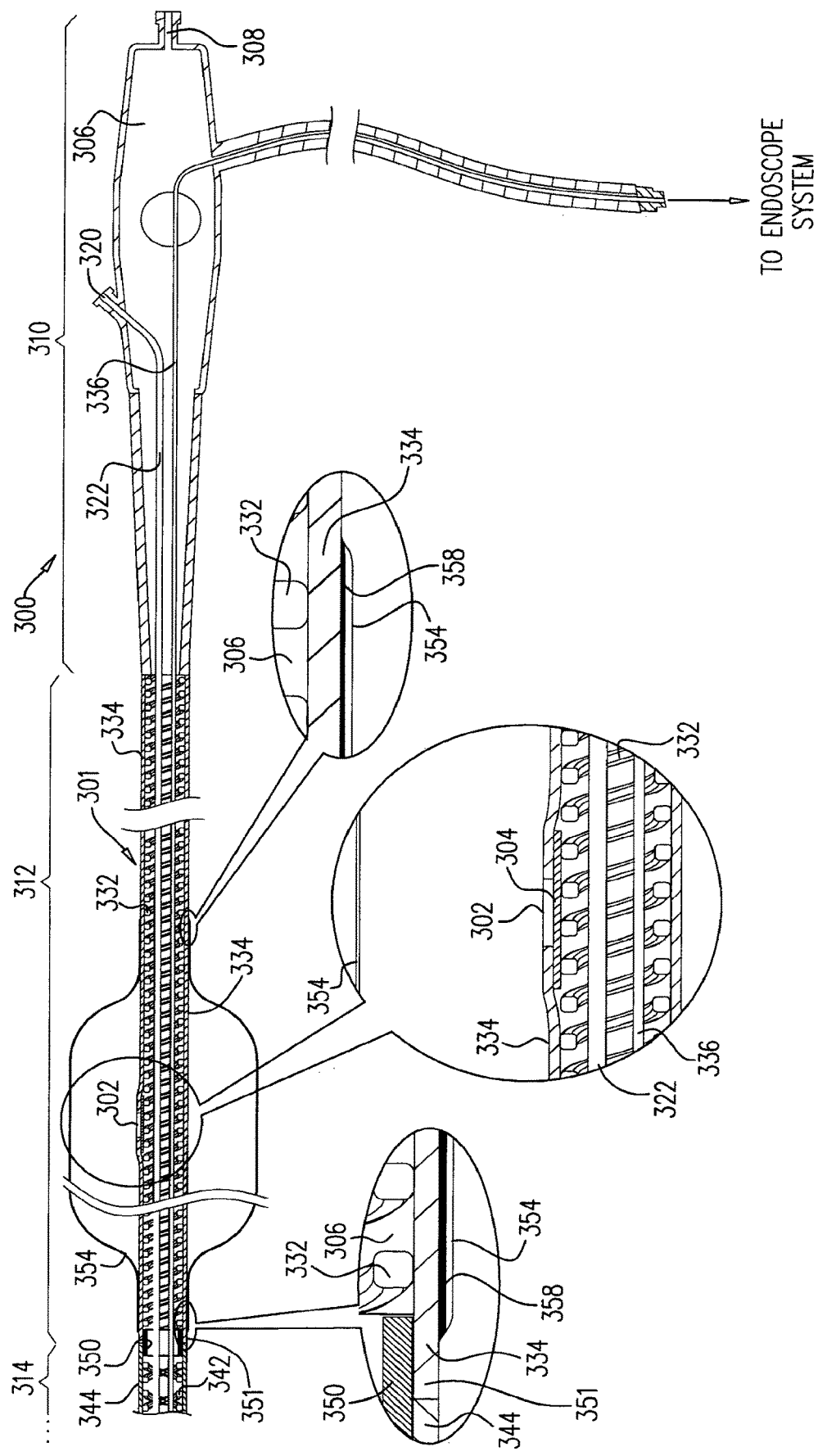

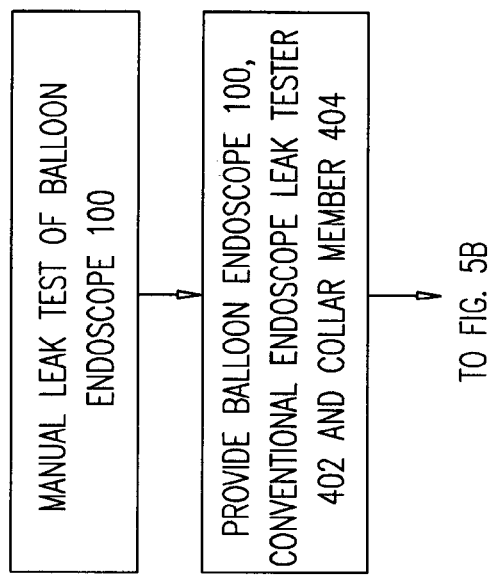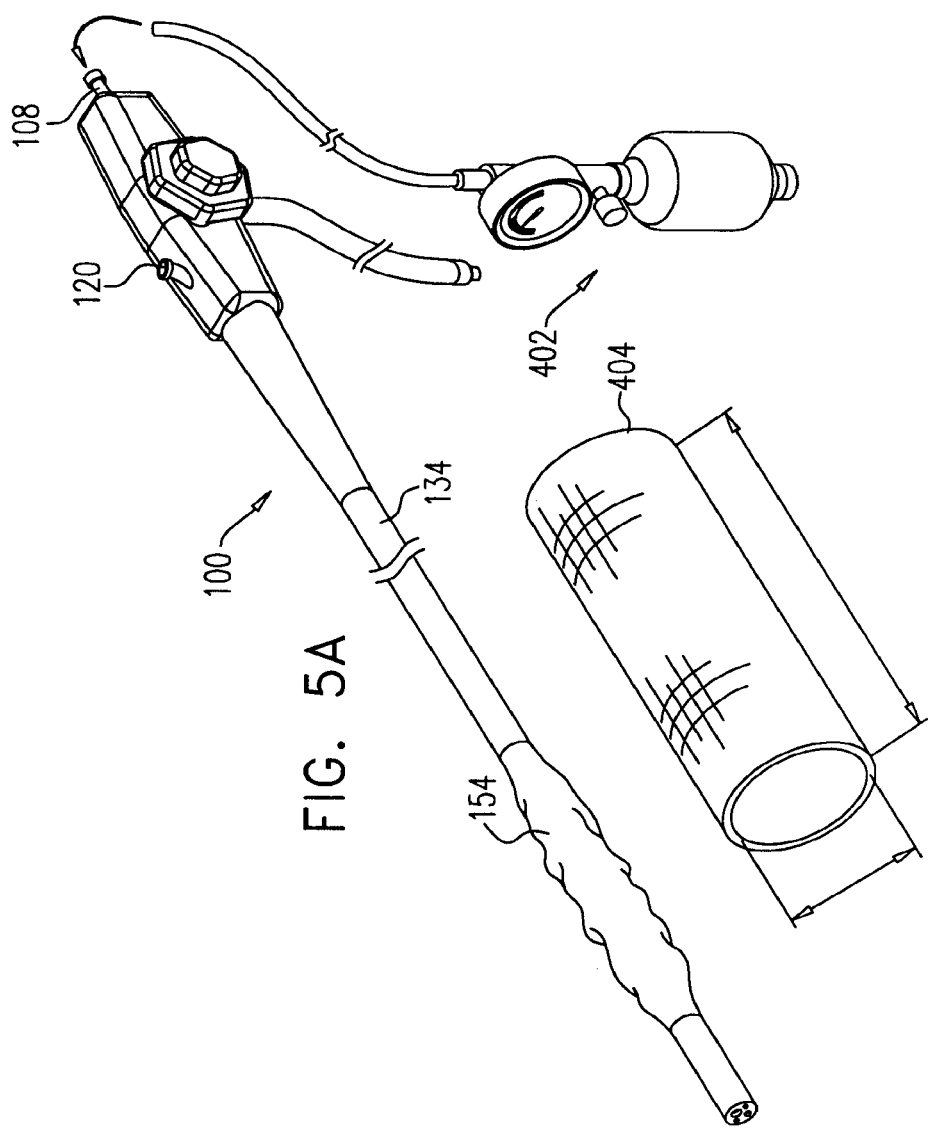

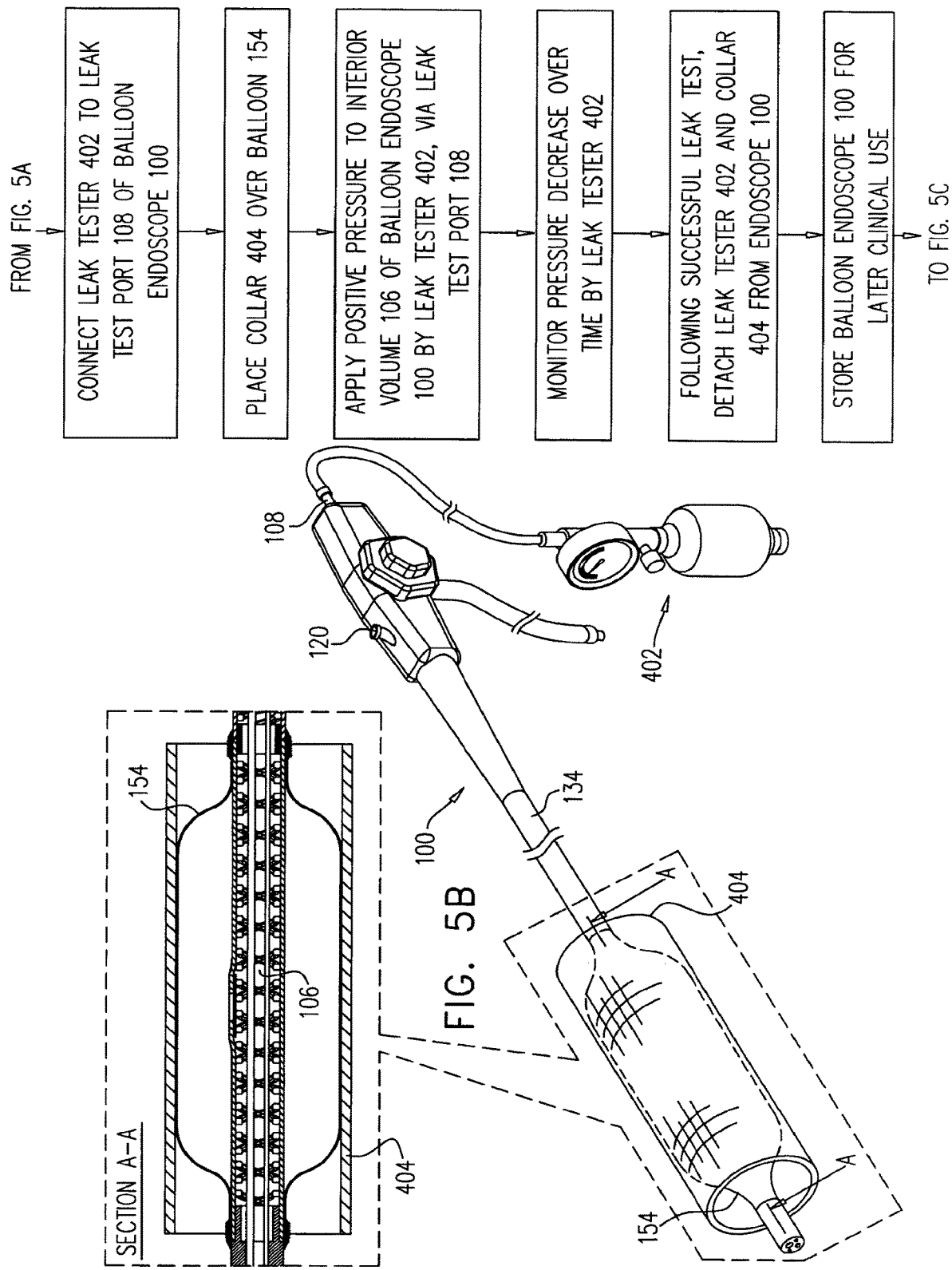

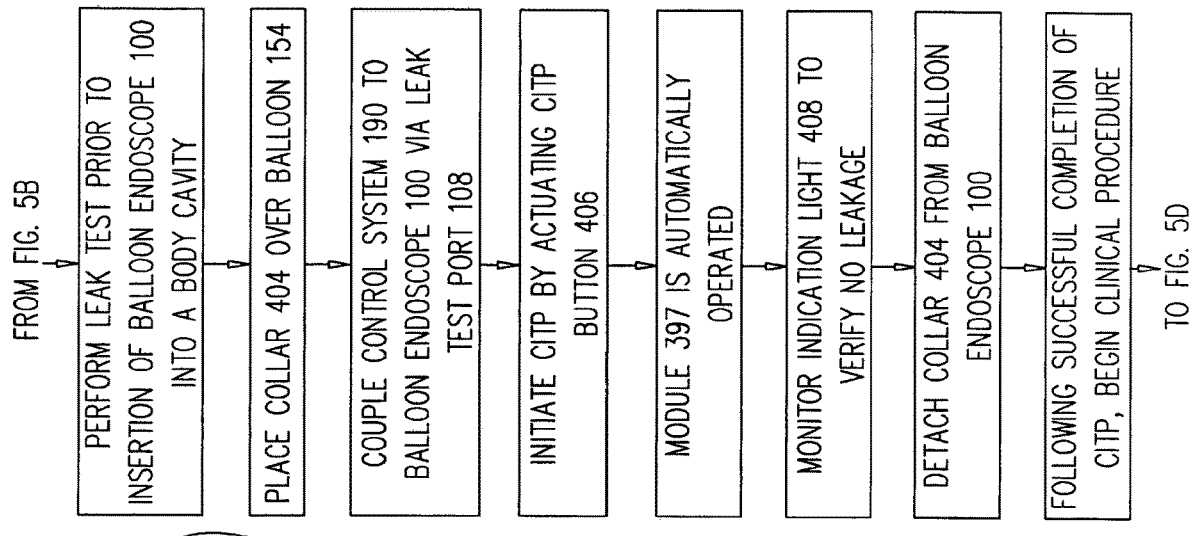
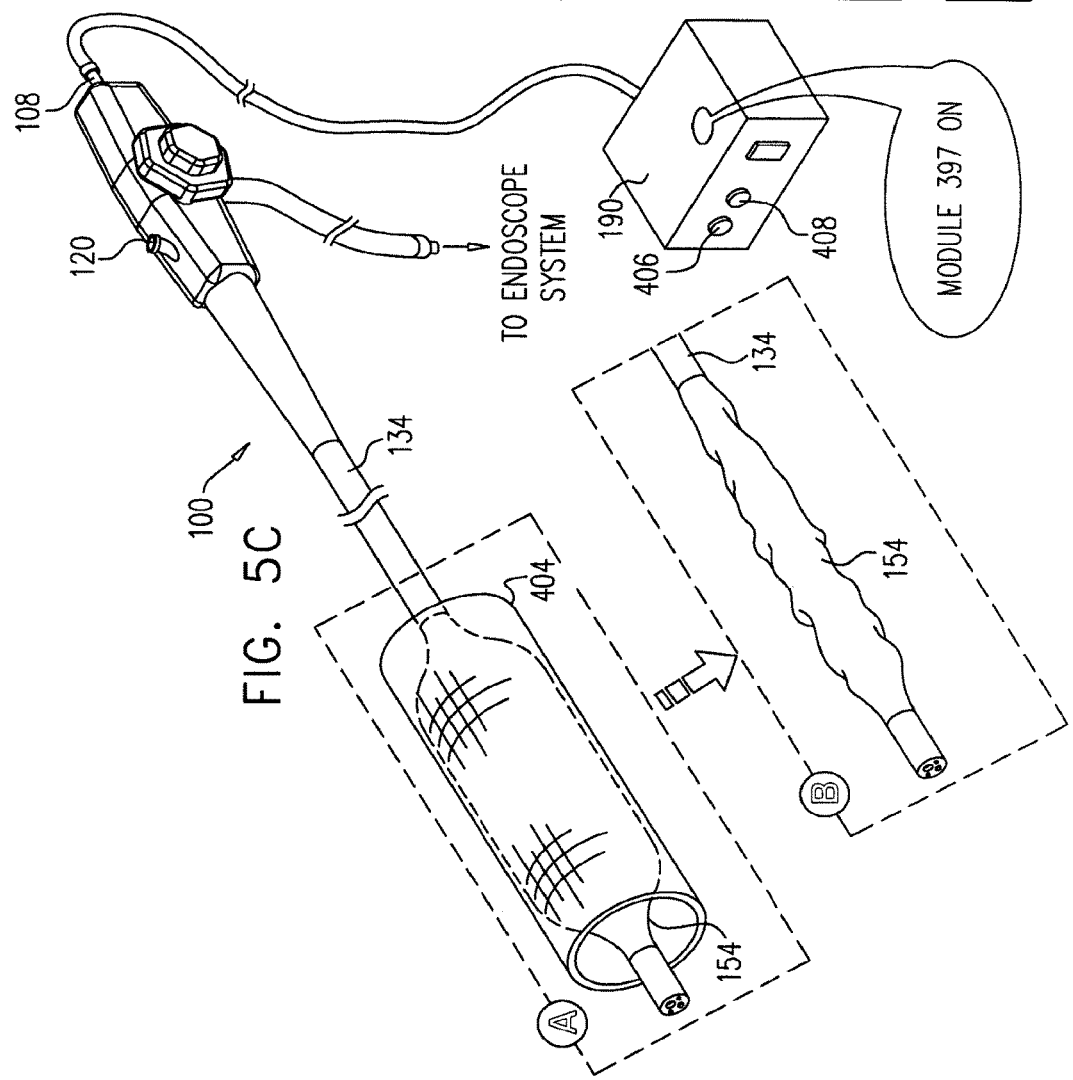
FIG. 5C

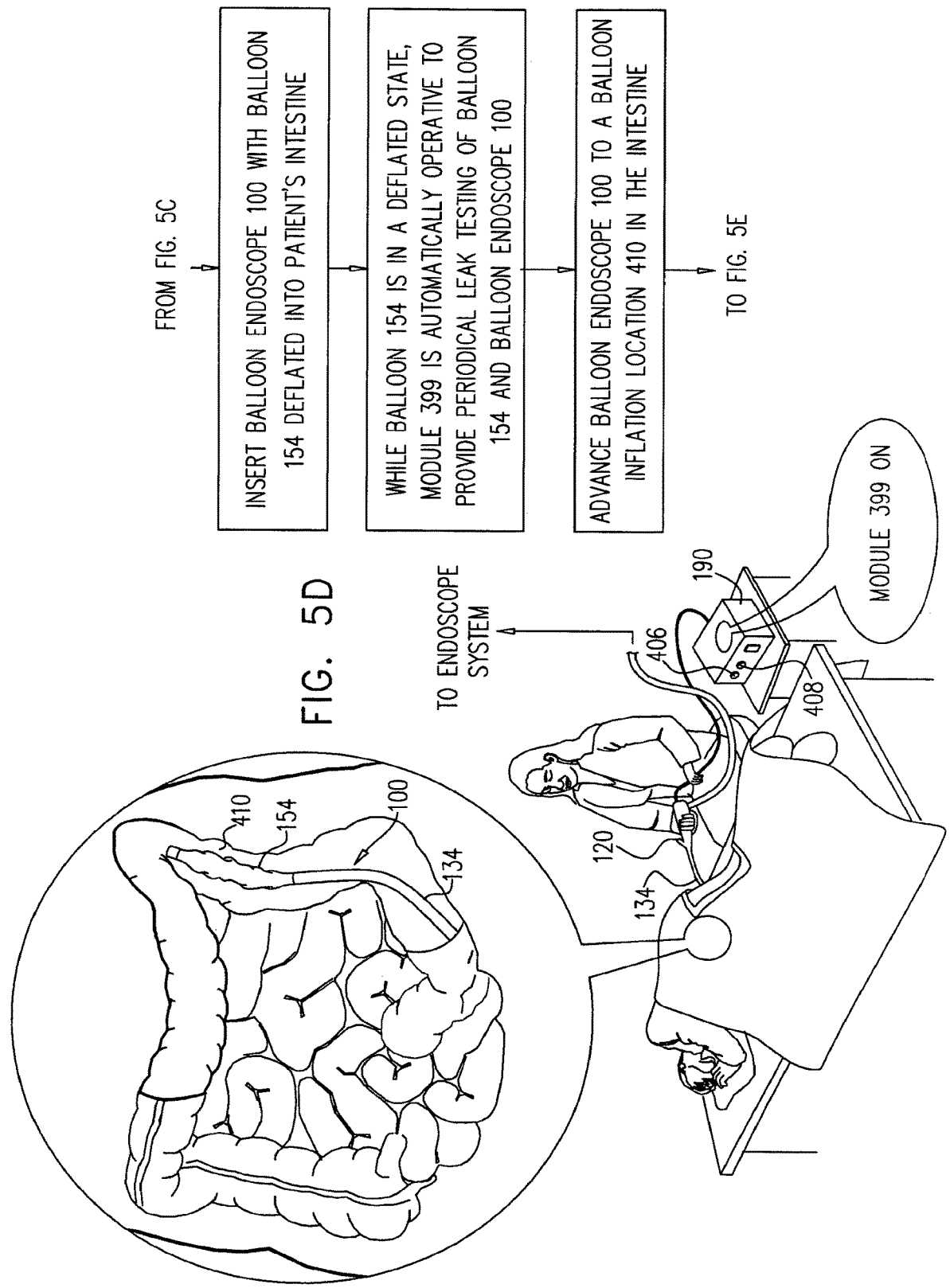

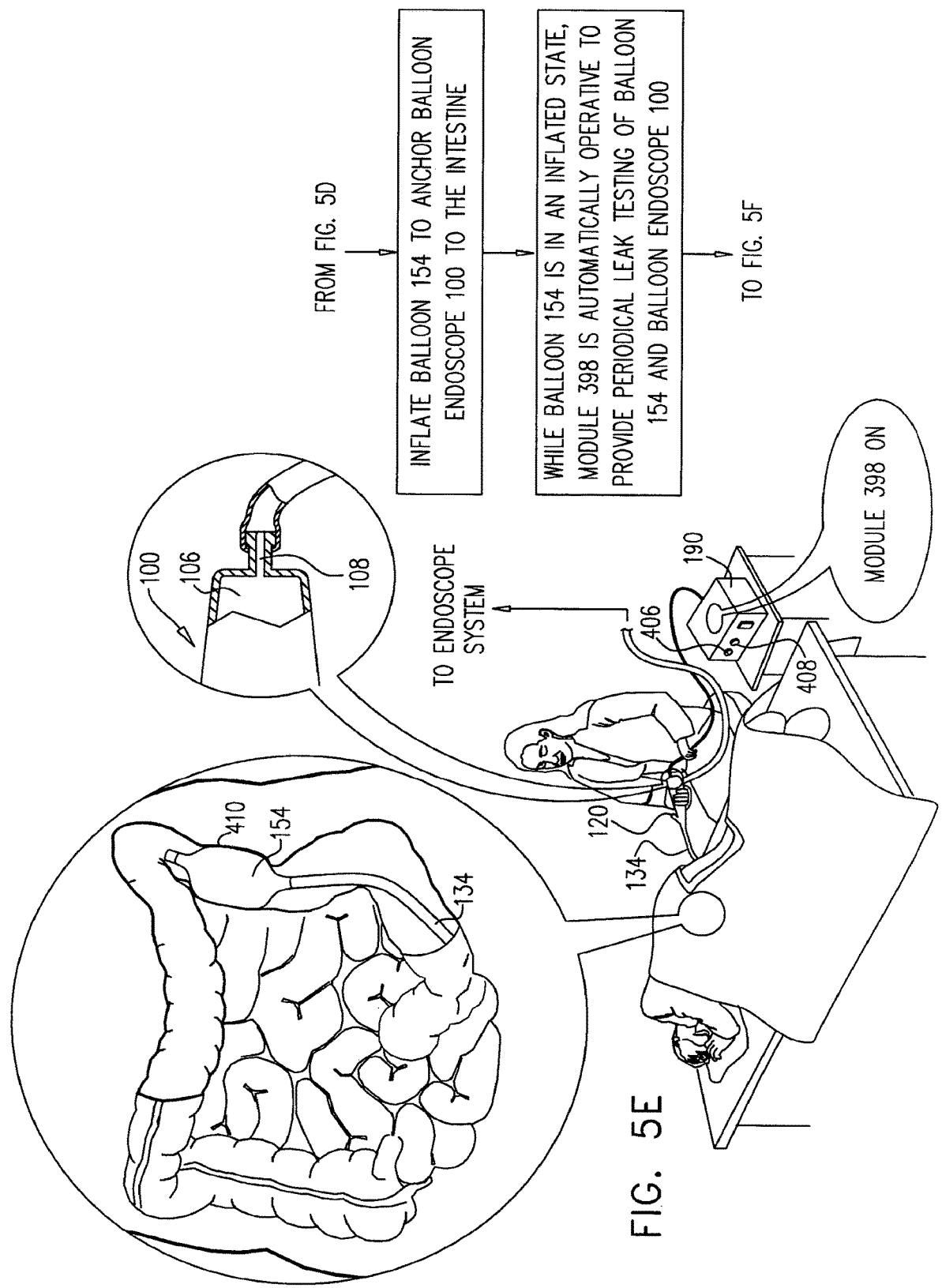

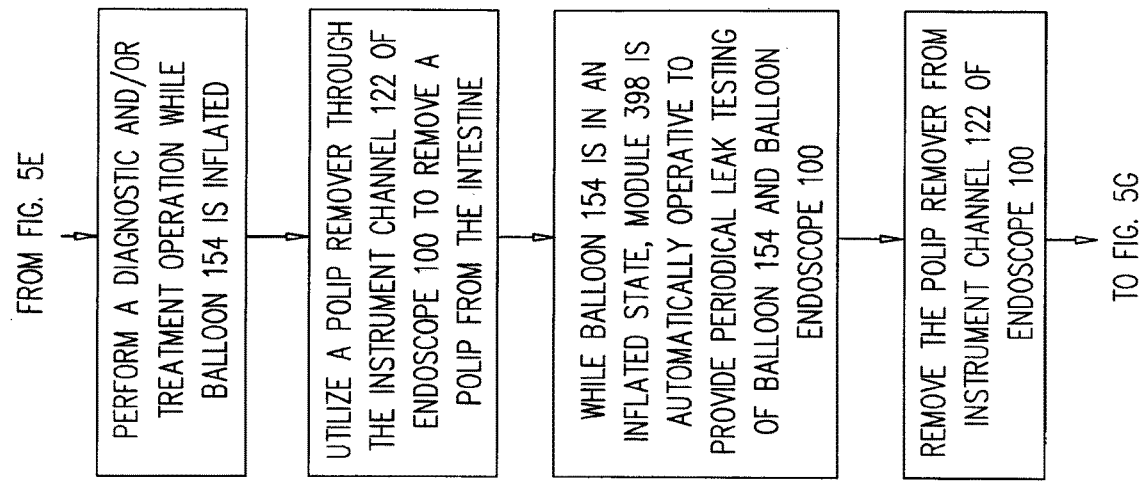
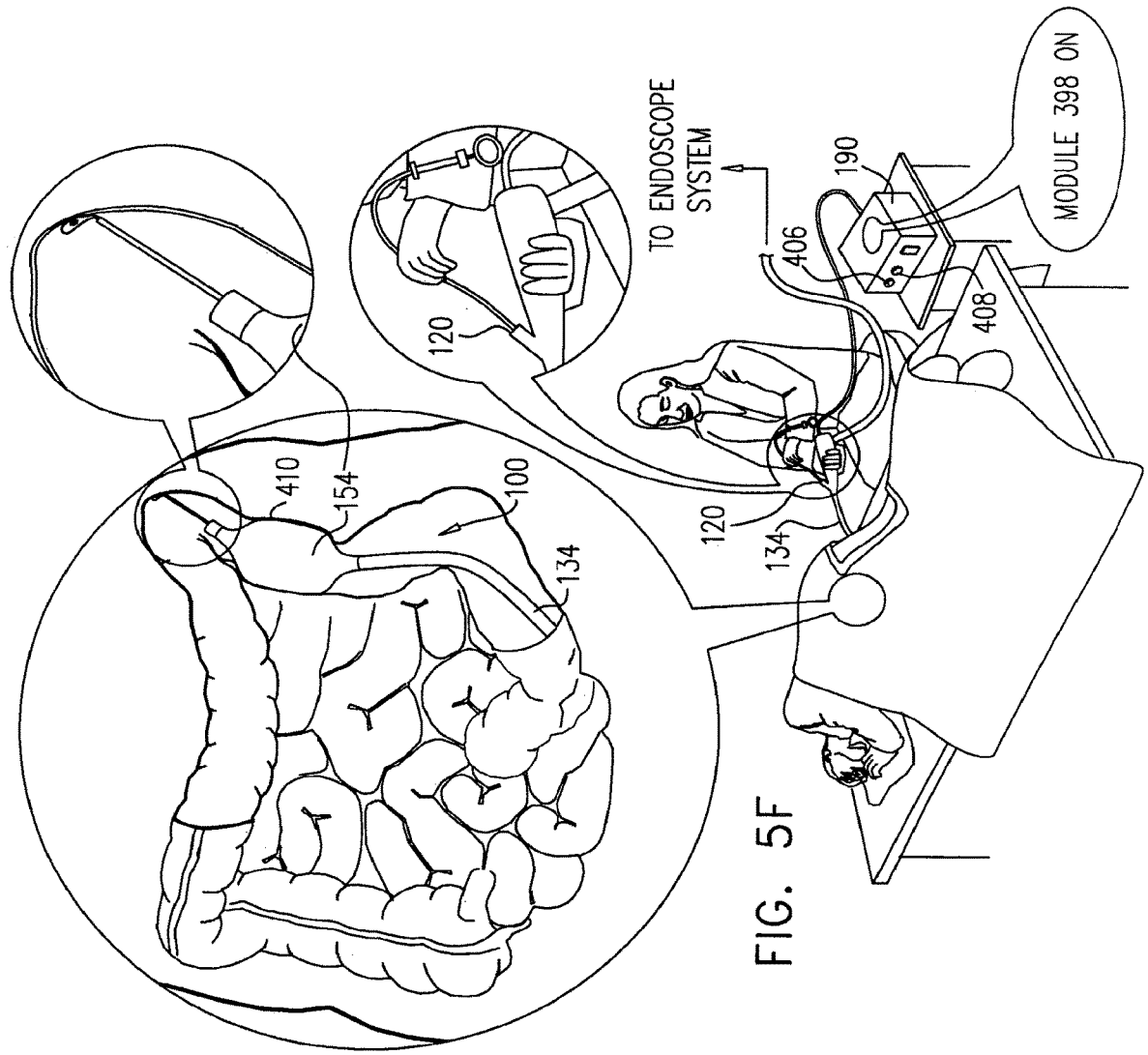
FIG. 5F

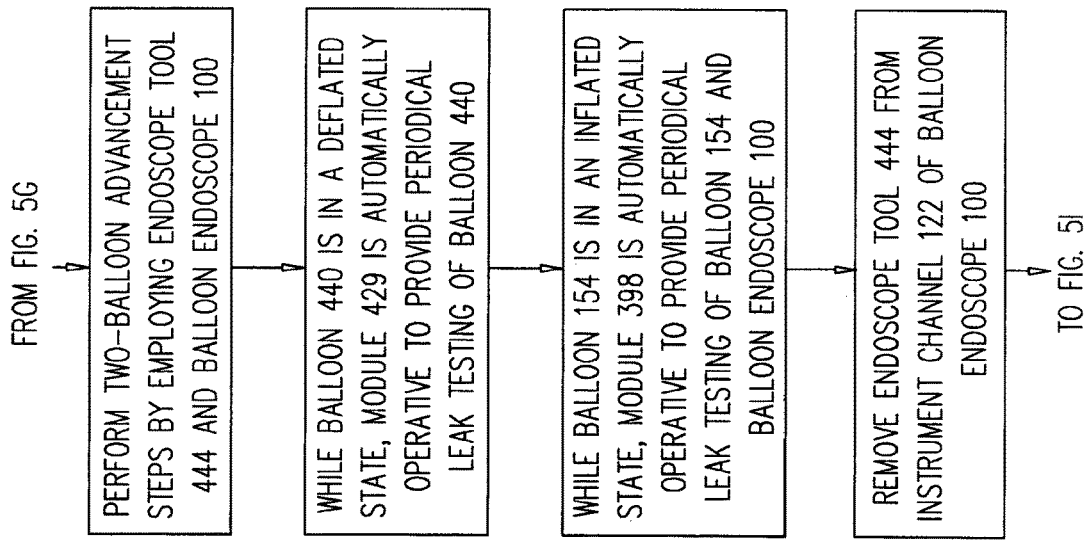
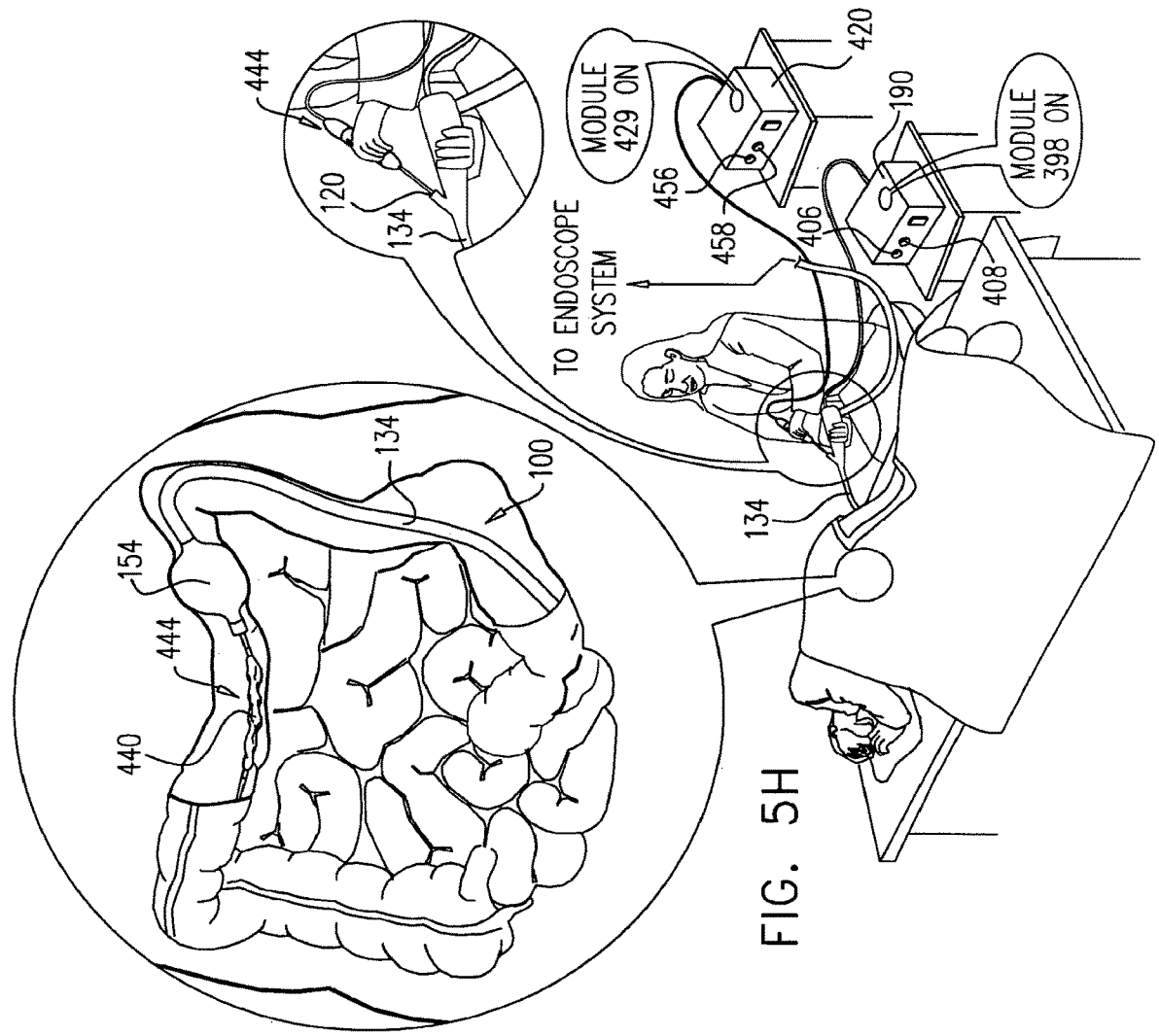
FIG. 5H

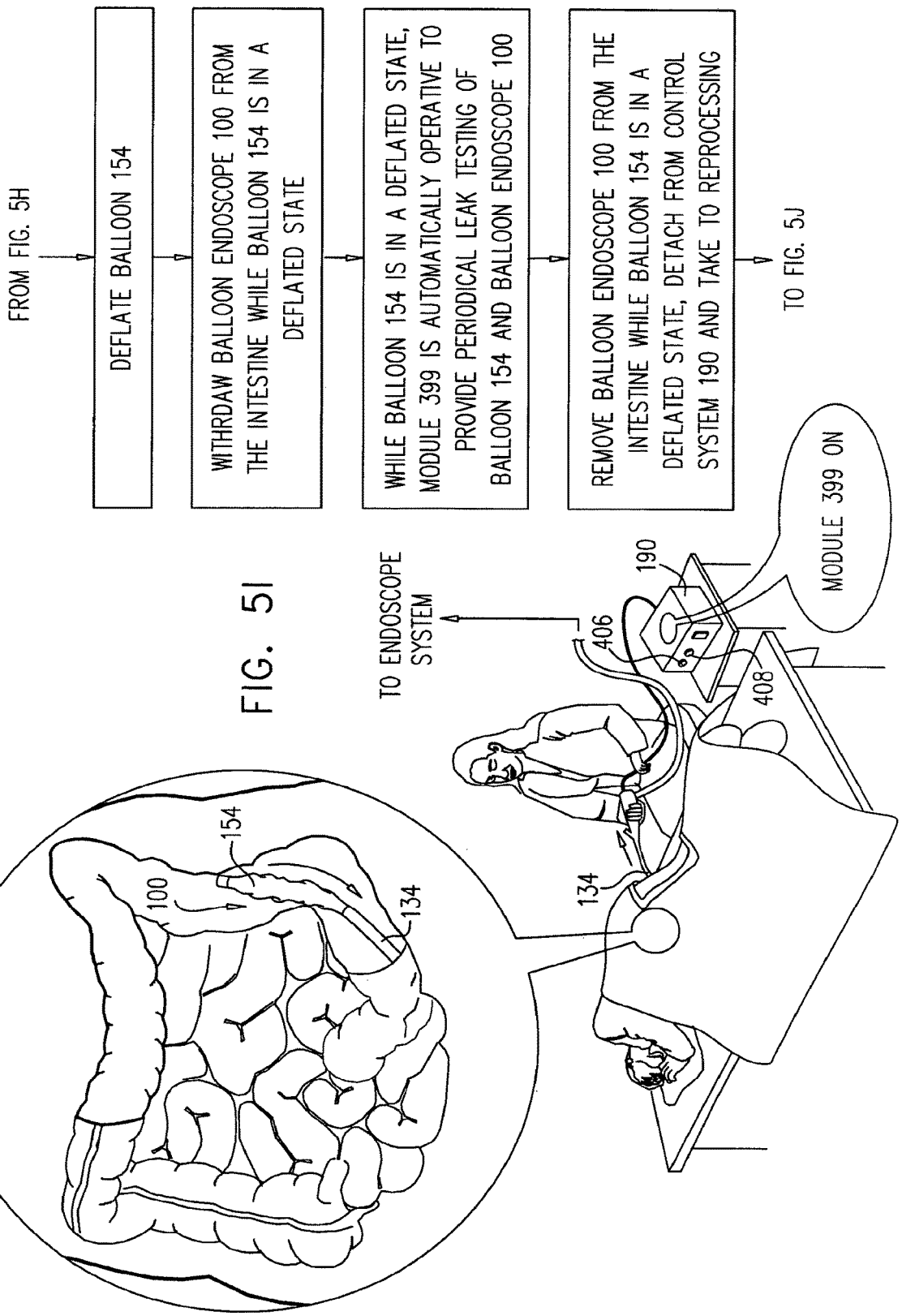

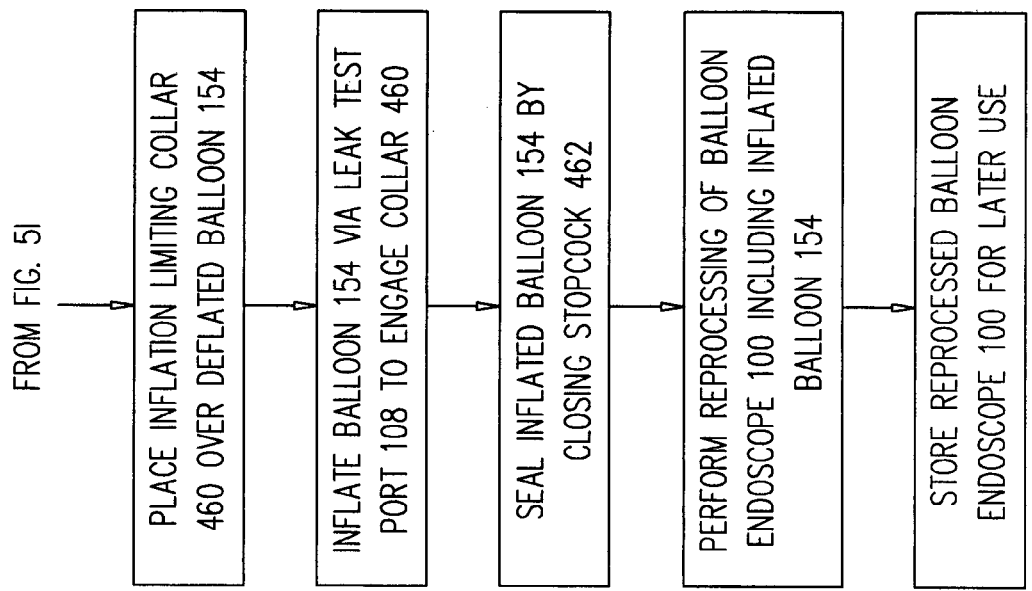
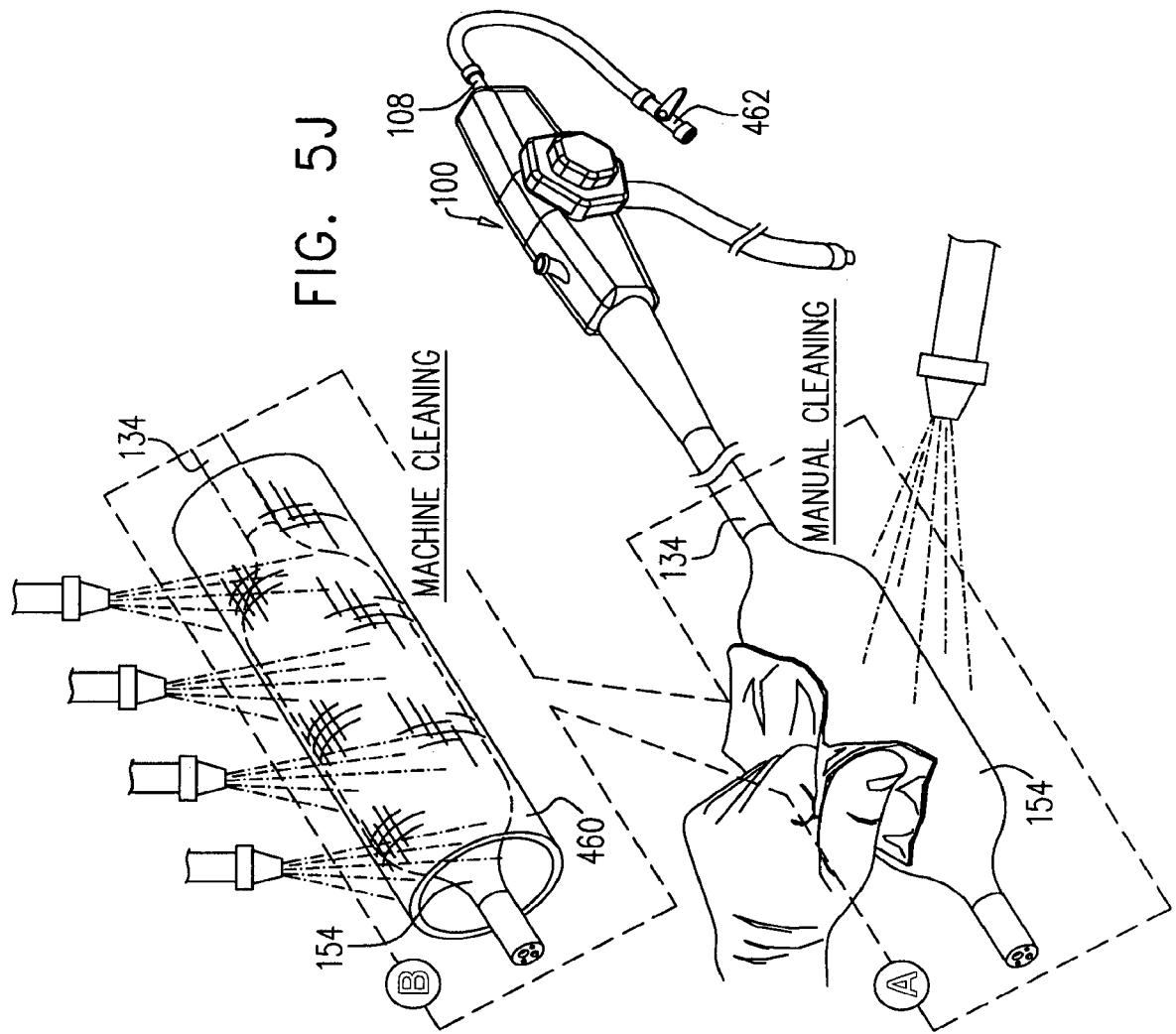
FIG. 5J

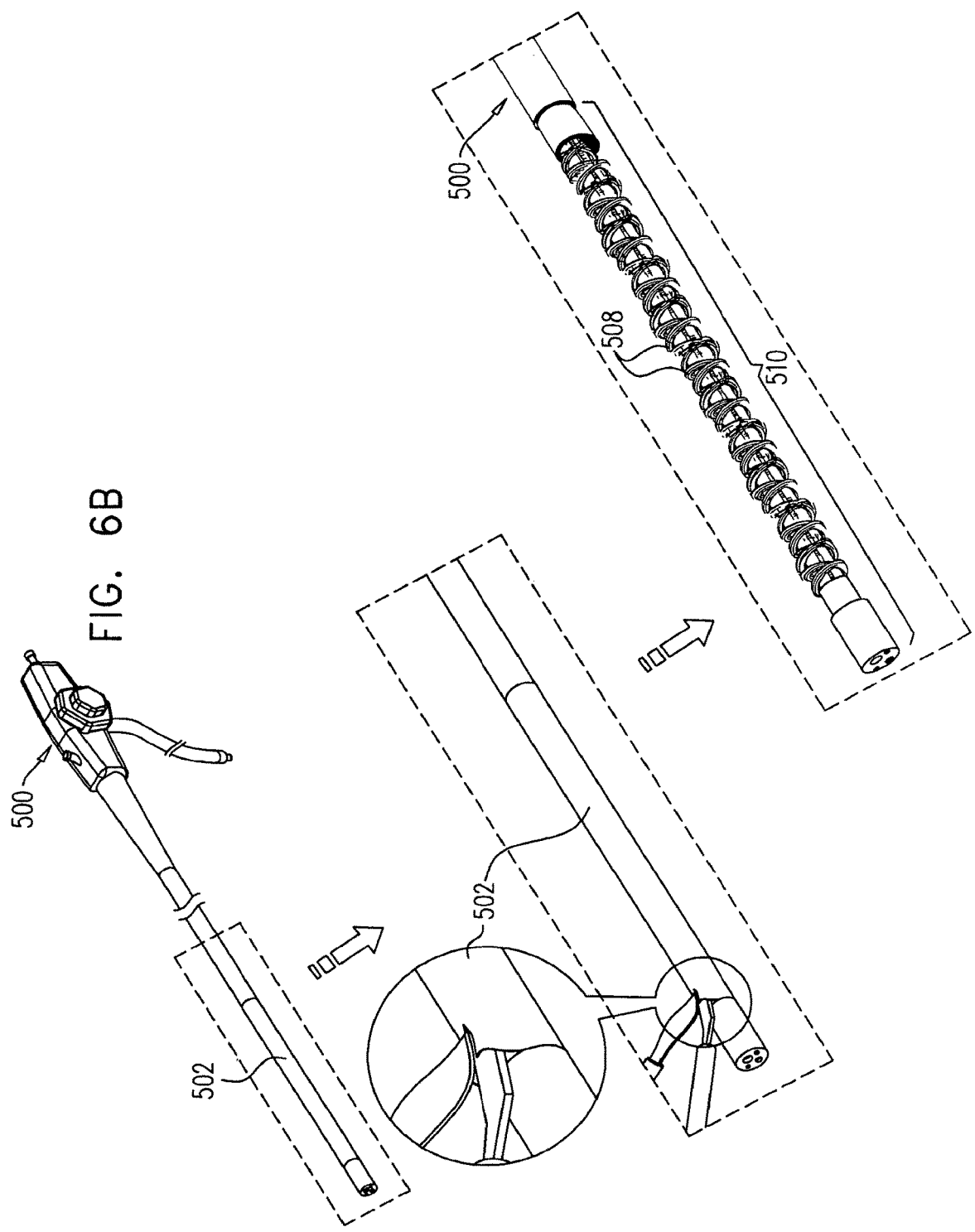

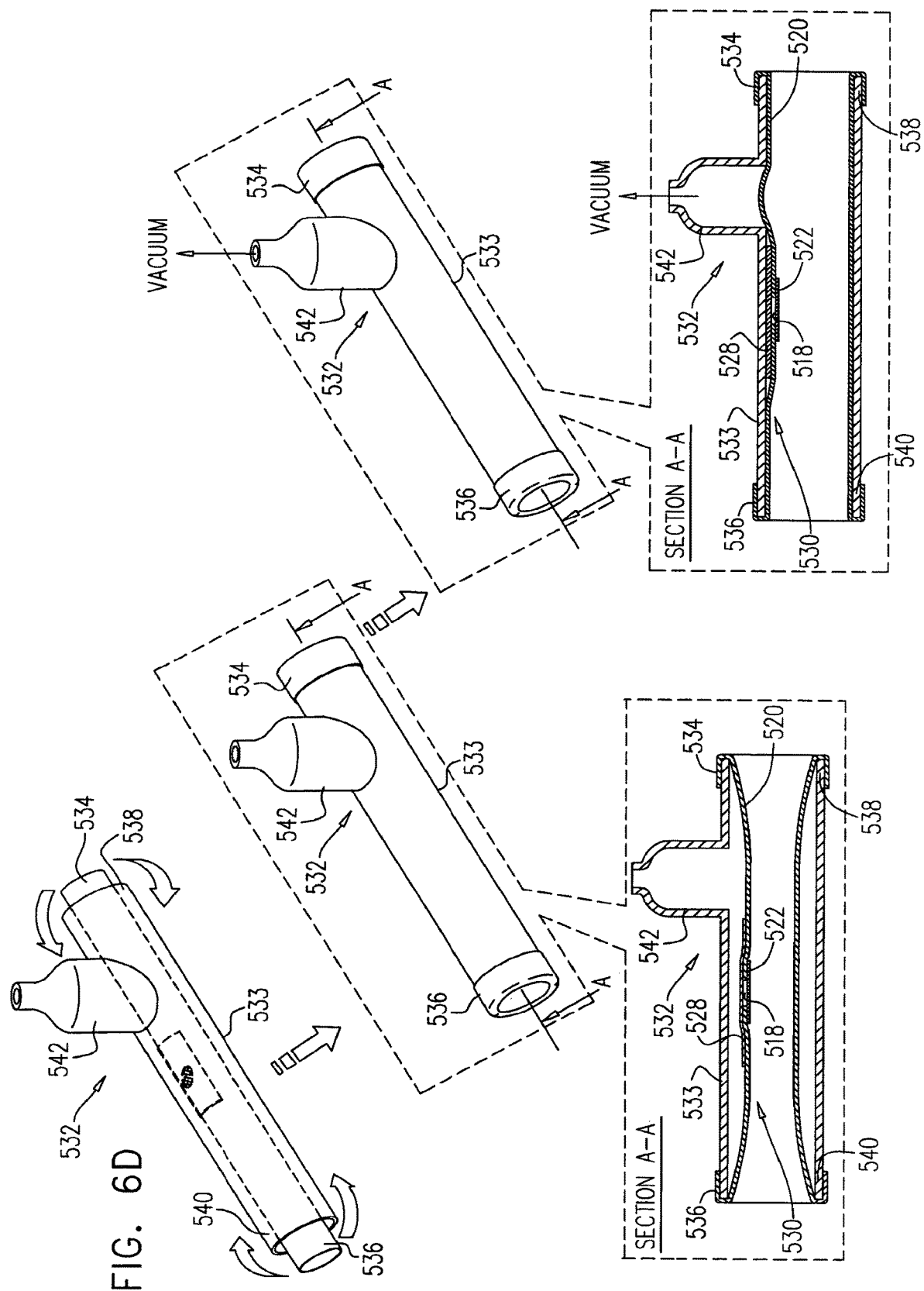

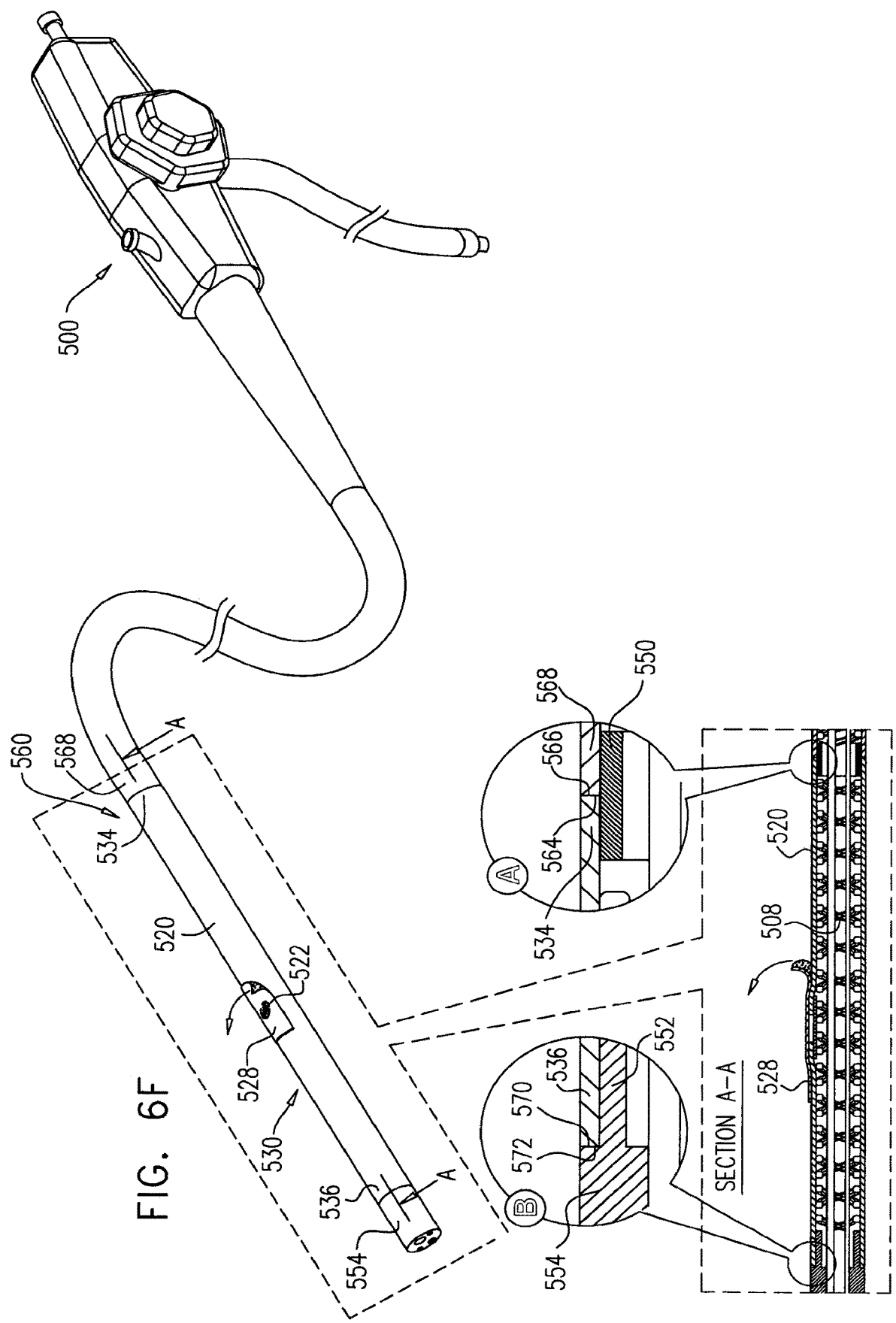

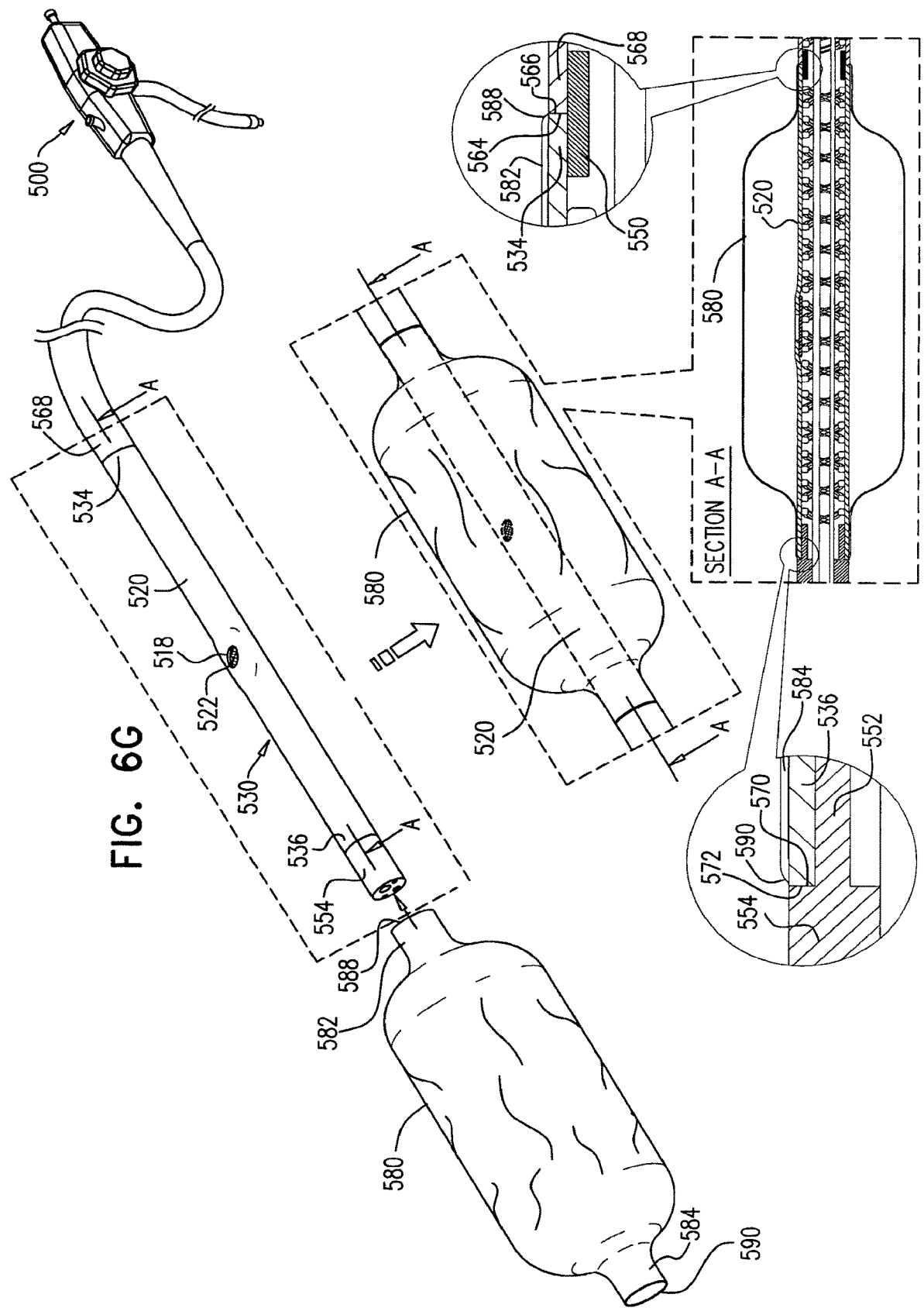

BALLOON ENDOSCOPE AND METHODS OF MANUFACTURE AND USE THEREOF

REFERENCE TO RELATED APPLICATIONS

This application is a divisional of U.S. application Ser. No. 13/583,634, filed Sep. 9, 2012, entitled "Balloon endoscope and methods of manufacture and use thereof," which is a National Phase of PCT Application PCT/IL2011/000222, filed Mar. 9, 2011, entitled "Balloon endoscope and methods of manufacture and use thereof," which claims priority to U.S. Provisional Patent Application Ser. No. 61/282,623, filed Mar. 9, 2010 and entitled "Endoscope with external fluid communication," U.S. Provisional Patent Application Ser. No. 61/282,624, filed Mar. 9, 2010 and entitled "Balloon Endoscope with internal fluid communication," U.S. Provisional Patent Application Ser. No. 61/344,690, filed Sep. 14, 2010 and entitled "Endoscope with External Gas Communication," and U.S. Provisional Patent Application Ser. No. 61/457,236, filed Feb. 9, 2011 and entitled "Manufacturing Methods of Balloon Endoscope with External Fluid Communication," the disclosures of which are hereby incorporated by reference and priorities of which are hereby claimed pursuant to 35 U.S.C. 33 CFR 1.38(a) (4) and (5)(i). The present application is a divisional of U.S. application Ser. No. 13/583,634, in which a Restriction Requirement was mailed Apr. 4, 2014. The present application is directed to Group II identified in the Restriction Requirement, drawn to a method for manufacture of a balloon endoscope.

Reference is also made to applicant's copending PCT Application No. PCT/IL2005/000152, filed Feb. 7, 2005; PCT Application No. PCT/IL2005/000849, filed Aug. 8, 2005; PCT Application No. PCT/IL2007/000600, filed May 17, 2007; PCT Application No. PCT/IL2007/000832, filed Jul. 4, 2007; PCT Application No. PCT/IL2008/000687, filed May 20, 2008; PCT Application No. PCT/IL2009/000322, filed Mar. 23, 2009; PCT Application No. PCT/IL2009/000940, filed Oct. 1, 2009; and PCT Application No. PCT/IL2010/000425, filed May 30, 2010, the disclosures of which are hereby incorporated by reference.

FIELD OF THE INVENTION

The present invention relates to endoscopy generally and more particularly to balloon endoscopes.

BACKGROUND OF THE INVENTION

The following patent publications and commercially available products are believed to represent the current state of the art:

U.S. Pat. Nos. 3,837,347; 4,040,413; 4,148,307; 4,176,662; 4,195,637; 4,261,339; 4,453,545; 4,616,652; 4,676,228; 4,862,874; 4,917,088; 5,135,487; 5,259,366; 5,593,419; 6,007,482; 6,461,294; 6,585,639; 6,663,589; and 6,702,735;

U.S. Patent Application publication Nos. 2003/0244361; 2004/0102681; 2005/0124856; 2005/0125005; 2005/0133453; 2005/0137457; 2005/0165233; 2005/0165273; 2005/0171400; 2006/0111610; and 2006/0161044;

Japanese Patent Application publication No. JP2003-250896;

Published PCT Patent Applications WO 2005/074377; WO 2005/017854; WO 2007/135665; WO 2008/004228; WO 2008/142685; WO 2009/122395; WO 2010/046891; WO 2010/137025; and Double Balloon Endoscope product, including EC-450B15 colonoscope, TS-13101 overtube and BS-2 front balloon, which interface with balloon pump controller BP-20 and EPX-4400HD video system, all commercially available from Fujinon Inc., of 10 High Point Drive, Wayne, N.J., USA; and, Single Balloon Endoscope product, including SIF-Q180 enteroscope, ST-SB1 overtube, which interface with balloon pump control OBCU and EVIS EXERA 11 system video system, all commercially available from Olympus Inc., of 3500 Corporate Parkway Center Valley, Pa. 18034-0610, USA.

SUMMARY OF THE INVENTION

The present invention seeks to provide improved balloon endoscopes and method of manufacture thereof.

There is thus provided in accordance with a preferred embodiment of the present invention a balloon endoscope including an endoscope body having a selectably pressurizable interior volume, which generally fills the interior of the endoscope body and a selectably inflatable balloon located on an outer surface of the endoscope body and defining a balloon volume which communicates with the interior volume for selectable inflation of the balloon by selectable pressurization of the interior volume.

Preferably, at least one conduit extends through at least part of the selectably pressurizable interior volume.

In accordance with a preferred embodiment of the present invention at least one fluid conduit extends through at least part of the selectably pressurizable interior volume and is sealed therefrom.

Preferably, the at least one conduit includes an instrument channel. Additionally or alternatively, the endoscope body includes a leak test port communicating with the selectably pressurizable interior volume. Alternatively or additionally, the balloon endoscope also includes a fluid flow discriminator at a forward portion of the selectably pressurizable interior volume which prevents passage of liquid but permits passage of gas therethrough.

Preferably, the balloon endoscope also includes a balloon inflation/deflation control system communicating with the selectably pressurizable interior volume and with the selectably inflatable balloon and being operative to provide automatic leak testing of at least one of the selectably pressurizable interior volume and the selectably inflatable balloon. Additionally, the balloon inflation/deflation control system has at least two modes of operation including a positive pressure leak testing mode and a negative pressure leak testing mode.

In accordance with a preferred embodiment of the present invention the selectably inflatable balloon is retrofitted onto the endoscope body. Additionally or alternatively, the selectably inflatable balloon includes generally cylindrical rearward and forward ends having a fixed inner cross-sectional radius R1, a central cylindrical portion having a fixed inner cross-sectional radius R2, when inflated to a nominal pressure, slightly in excess of atmospheric pressure, and circularly symmetric tapered portions extending between the central cylindrical portion and each of the rearward and forward ends, whose inner radius changes from R2 to R1 where cos(Alpha) is approximately equal to r/R2, r is the inner radius of the balloon at a given location between the central cylindrical portion and one of the rearward and forward ends; and Alpha is the angle between a tangent to the balloon at the given location and a longitudinal axis of symmetry of the balloon.

Preferably, the selectably inflatable balloon is integrally formed as part of an outer sheath of the endoscope. In accordance with a preferred embodiment of the present invention the balloon endoscope also includes a bending section including a bending rubber sheath and the selectably inflatable balloon is located rearwardly of the bending rubber sheath.

Preferably, the selectably inflatable balloon is removably mounted onto the outer surface of the endoscope. In accordance with a preferred embodiment of the present invention the balloon endoscope also includes a bending section including a bending rubber sheath and wherein the selectably inflatable balloon overlies the bending rubber sheath. Additionally, the selectably inflatable balloon is generally coextensive with the bending rubber sheath.

There is also provided in accordance with another preferred embodiment of the present invention a balloon endoscope including an endoscope body having a leak test port and a selectably inflatable balloon associated with the endoscope body and defining a balloon volume which communicates with the leak test port.

Preferably, the endoscope body has a selectably pressurizable interior volume, which generally fills the interior of the endoscope body. Additionally or alternatively, the selectably inflatable balloon is located on an outer surface of the endoscope body. Alternatively or additionally, the balloon volume communicates with the interior volume for selectable inflation of the balloon by selectable pressurization of the interior volume via the leak test port.

In accordance with a preferred embodiment of the present invention at least one conduit extends through at least part of the selectably pressurizable interior volume. Preferably, at least one fluid conduit extends through at least part of the selectably pressurizable interior volume and is sealed therefrom. Additionally, the at least one conduit includes an instrument channel.

Preferably, the balloon endoscope also includes a fluid flow discriminator communicating with the balloon volume, which prevents passage of liquid but permits passage of gas therethrough. Additionally or alternatively, the balloon endoscope also includes a balloon inflation/deflation control system communicating with the balloon volume and being operative to provide automatic leak testing of the selectably inflatable balloon. Additionally, the balloon inflation/deflation control system has at least two modes of operation including a positive pressure leak testing mode and a negative pressure leak testing mode.

In accordance with a preferred embodiment of the present invention the selectably inflatable balloon is retrofitted onto the endoscope body. Additionally or alternatively, the selectably inflatable balloon includes generally cylindrical rearward and forward ends having a fixed inner cross-sectional radius R1, a central cylindrical portion having a fixed inner cross-sectional radius R2, when inflated to a nominal pressure, slightly in excess of atmospheric pressure, and circularly symmetric tapered portions extending between the central cylindrical portion and each of the rearward and forward ends, whose inner radius changes from R2 to R1 where cos(Alpha) is approximately equal to r/R2, r is the inner radius of the balloon at a given location between the central cylindrical portion and one of the rearward and forward ends and Alpha is the angle between a tangent to the balloon at the given location and a longitudinal axis of symmetry of the balloon.

Preferably, the selectably inflatable balloon is integrally formed as part of an outer sheath of the endoscope. In accordance with a preferred embodiment of the present invention the balloon endoscope also includes a bending section including a bending rubber sheath and the selectably inflatable balloon is located rearwardly of the bending rubber sheath.

In accordance with a preferred embodiment of the present invention the selectably inflatable balloon is removably mounted onto an outer surface of the endoscope. Additionally or alternatively, the balloon endoscope also includes a bending section including a bending rubber sheath and the selectably inflatable balloon overlies the bending rubber sheath. In accordance with a preferred embodiment of the present invention the selectably inflatable balloon is generally coextensive with the bending rubber sheath.

There is further provided in accordance with yet another preferred embodiment of the present invention an endoscope including an endoscope body having a forward portion and a rearward portion and a fluid passageway extending from the rearward portion to the forward portion and including a fluid flow discriminator at the forward portion which prevents passage of liquid but permits passage of gas.

Preferably, the fluid passageway includes an interior volume of the endoscope body, which generally fills the interior of the endoscope body. In accordance with a preferred embodiment of the present invention the fluid passageway includes a conduit extending through an interior volume of the endoscope body, which interior volume generally fills the interior of the endoscope body.

In accordance with a preferred embodiment of the present invention the fluid passageway includes a conduit. Preferably, the fluid passageway communicates with a leak test port of the endoscope.

In accordance with a preferred embodiment of the present invention the endoscope also includes a selectably inflatable balloon located on an outer surface of the endoscope body and defining a balloon volume which communicates with the fluid passageway for selectable inflation of the balloon. Additionally the selectably inflatable balloon is removably mounted onto the outer surface of the endoscope body.

In accordance with a preferred embodiment of the present invention the fluid flow discriminator includes a gas permeable, liquid impermeable filter. Additionally or alternatively, the endoscope also includes a balloon inflation/deflation control system communicating with the fluid passageway.

Preferably, the selectably inflatable balloon is retrofitted onto the endoscope body. In accordance with a preferred embodiment of the present invention the selectably inflatable balloon includes generally cylindrical rearward and forward ends having a fixed inner cross-sectional radius R1, a central cylindrical portion having a fixed inner cross-sectional radius R2, when inflated to a nominal pressure, slightly in excess of atmospheric pressure, and circularly symmetric tapered portions extending between the central cylindrical portion and each of the rearward and forward ends, whose inner radius changes from R2 to R1 where cos(Alpha) is approximately equal to r/R2, r is the inner radius of the balloon at a given location between the central cylindrical portion and one of the rearward and forward ends and Alpha is the angle between a tangent to the balloon at the given location and a longitudinal axis of symmetry of the balloon.

In accordance with a preferred embodiment of the present invention the selectably inflatable balloon is integrally formed as part of an outer sheath of the endoscope. Preferably, the balloon endoscope also includes a bending section including a bending rubber sheath and the selectably inflatable balloon is located rearwardly of the bending rubber sheath.

Preferably, the balloon endoscope also includes a bending section including a bending rubber sheath and wherein the selectably inflatable balloon overlies the bending rubber sheath. Additionally, the selectably inflatable balloon is generally coextensive with the bending rubber sheath.

There is yet further provided in accordance with still another preferred embodiment of the present invention a balloon endoscope including an endoscope body having a selectably pressurizable interior volume, which generally fills the interior of the endoscope body, a selectably inflatable balloon located on an outer surface of the endoscope body and a balloon inflation/deflation control system communicating with the selectably pressurizable interior volume and with the selectably inflatable balloon and being operative to provide automatic leak testing of at least one of the selectably pressurizable interior volume and the selectably inflatable balloon.

Preferably, the balloon inflation/deflation control system has at least two modes of operation including a positive pressure leak testing mode and a negative pressure leak testing mode.

In accordance with a preferred embodiment of the present invention the balloon inflation/deflation control system includes at least one of the following operational modules: an initialization module, operable prior to an endoscopy procedure, a real time leak monitoring balloon inflation module, operable during an endoscopy procedure and a real time leak monitoring balloon deflation module, operable during an endoscopy procedure.

More preferably, the balloon inflation/deflation control system includes at least two of the following operational modules: an initialization module, operable prior to an endoscopy procedure, a real time leak monitoring balloon inflation module, operable during an endoscopy procedure and a real time leak monitoring balloon deflation module, operable during an endoscopy procedure. Most preferably, the balloon inflation/deflation control system includes the following operational modules: an initialization module, operable prior to an endoscopy procedure, a real time leak monitoring balloon inflation module, operable during an endoscopy procedure and a real time leak monitoring balloon deflation module, operable during an endoscopy procedure.

In accordance with a preferred embodiment of the present invention the initialization module includes the following functionality: balloon endoscope pressurization producing balloon inflation, pressure leak test when the balloon endoscope is in a pressurized state and the balloon is surrounded by a balloon confining, gas permeable collar member, balloon endoscope depressurization producing balloon deflation, vacuum leak test when the balloon endoscope is in a pressurized state and provision of system go/no go indication.

Preferably, the real time leak monitoring balloon inflation module includes the following functionality: balloon endoscope pressurization producing balloon inflation, provision of complete balloon inflation indication, pressure leak test when the balloon endoscope is in a pressurized state within a body cavity and provision of leak indication.

In accordance with a preferred embodiment of the present invention the real time leak monitoring balloon deflation module includes the following functionality: balloon endoscope depressurization producing balloon deflation, provision of complete balloon deflation indication to the operator, pressure leak test when the balloon endoscope is in a depressurized state within a body cavity and provision of leak indication.

Preferably, the balloon endoscope also includes an endoscope tool balloon and the balloon inflation/deflation control system includes: an endoscope balloon inflation/deflation control system sub-system communicating with the selectably pressurizable interior volume and with the selectably inflatable balloon and being operative to provide automatic leak testing of at least one of the selectably pressurizable interior volume and the selectably inflatable balloon and an endoscope tool balloon inflation/deflation control system sub-system communicating with the endoscope tool balloon and being operative to provide automatic leak testing of the endoscope tool balloon.

In accordance with a preferred embodiment of the present invention the selectably inflatable balloon is retrofitted onto the endoscope body.

There is even further provided in accordance with another preferred embodiment of the present invention a method for balloon endoscopy including providing an endoscope including an endoscope body having a selectably pressurizable interior volume, which generally fills the interior of the endoscope body, and a selectably inflatable balloon and selectably inflating the selectably inflatable balloon by selectable pressurization of the interior volume.

Preferably, the selectably inflating includes selectably inflating the selectably inflatable balloon via a leak test port communicating with the selectably pressurizable interior volume. Additionally or alternatively, the selectably inflating includes enabling passage of gas but not liquid between the selectably pressurizable interior volume and the selectably inflatable balloon.

In accordance with a preferred embodiment of the present invention the selectably inflating includes providing automatic leak testing of at least one of the selectably pressurizable interior volume and the selectably inflatable balloon.

There is also provided in accordance with still another preferred embodiment of the present invention a method for balloon endoscopy including providing an endoscope including an endoscope body having a leak test port and a selectably inflatable balloon and selectably inflating the selectably inflatable balloon via the leak test port.

Preferably, the selectably inflating includes enabling passage of gas but not liquid between the selectably pressurizable interior volume and the the selectably inflatable balloon. Additionally or alternatively, the selectably inflating includes providing automatic leak testing of at least one of the selectably pressurizable interior volume and the selectably inflatable balloon.

There is further provided in accordance with yet another preferred embodiment of the present invention a method for balloon endoscopy including providing an endoscope having a forward portion and a rearward portion and a fluid passageway extending from the rearward portion to the forward portion and providing passage of gas but not liquid between the fluid passageway and a location outside the endoscope at the forward portion thereof.

In accordance with a preferred embodiment of the present invention the method for balloon endoscopy also includes selectably pressurizing the fluid passageway and providing gas communication between the fluid passageway and a balloon volume defined at the interior of a selectably inflatable balloon sealingly mounted over an outer surface of the forward portion of the endoscope.

There is still further provided in accordance with another preferred embodiment of the present invention a method for balloon endoscopy including providing an endoscope including an endoscope body having a selectably pressurizable interior volume and a selectably inflatable balloon located on an outer surface of the endoscope body and providing automatic leak testing of at least one of the selectably pressurizable interior volume and the selectably inflatable balloon.

There is even further provided in accordance with still another preferred embodiment of the present invention a method of manufacture of a balloon endoscope including providing an at least partially incomplete endoscope having a selectably pressurizable interior volume, providing at least one aperture in an outer sheath of the endoscope, the at least one aperture communicating with the selectably pressurizable interior volume and providing a selectably inflatable balloon over the outer sheath and in sealing engagement therewith, the balloon being arranged to have a balloon volume overlying the at least one aperture.

Preferably, the providing an at least partially incomplete endoscope includes providing an endoscope lacking at least part of the outer sheath and the providing at least one aperture includes forming an aperture in an outer sheath and thereafter mounting the outer sheath on the endoscope.

In accordance with a preferred embodiment of the present invention the method of manufacture of a balloon endoscope also includes associating a fluid flow discriminator with at least one aperture. Additionally or alternatively, the providing an at least partially incomplete endoscope includes retrofitting the endoscope to remove at least part of the outer sheath thereof.

There is still further provided in accordance with yet another preferred embodiment of the present invention a method of manufacture of an endoscope including providing an at least partially incomplete endoscope and providing at least one aperture in an outer sheath of the endoscope and associating a fluid flow discriminator with the at least one aperture.

In accordance with a preferred embodiment of the present invention the method of manufacture of an endoscope also includes providing a selectably inflatable balloon over the outer sheath and in sealing engagement therewith, the balloon being arranged to have a balloon volume overlying the at least one aperture. Additionally or alternatively, the providing an at least partially complete endoscope includes providing an endoscope lacking at least part of the outer sheath and the providing at least one aperture includes forming an aperture in an outer sheath and thereafter mounting the outer sheath on the endoscope.

There is even further provided in accordance with still another preferred embodiment of the present invention a method of reprocessing a balloon endoscope including inflating a balloon of the balloon endoscope and reprocessing the balloon endoscope while the balloon is inflated. Preferably, the method of reprocessing the balloon endoscope also includes, prior to inflating the balloon of the balloon endoscope, placing a liquid spray permeable inflation limiting collar over the balloon.

There is yet further provided in accordance with another preferred embodiment of the present invention an inflatable/deflatable balloon suitable for use as part of a balloon endoscope or balloon catheter and including generally cylindrical rearward and forward ends having a fixed inner cross-sectional radius R1, a central cylindrical portion having a fixed inner cross-sectional radius R2, when inflated to a nominal pressure, slightly in excess of atmospheric pressure, and circularly symmetric tapered portions extending between the central cylindrical portion and each of the rearward and forward ends, whose inner radius changes from R2 to R1 where: cos(Alpha) is approximately equal to r/R2, r is the inner radius of the balloon at a given location between the central cylindrical portion and one of the rearward and forward ends and Alpha is the angle between a tangent to the balloon at the given location and a longitudinal axis of symmetry of the balloon.

BRIEF DESCRIPTION OF THE DRAWINGS

The present invention will be understood and appreciated from the following detailed description, taken in conjunction with the drawings in which:

FIGS. 2A & 2B illustrate a second embodiment of a balloon endoscope constructed and operative in accordance with the present invention;

FIGS. 3A & 3B illustrate a third embodiment of a balloon endoscope constructed and operative in accordance with the present invention;

FIGS. 5A-5J are together a simplified pictorial flowchart which illustrates operation of a balloon endoscope in accordance with a preferred embodiment of the present invention; and FIGS. 6A-6I are simplified pictorial illustrations of a method of manufacture of a balloon endoscope in accordance with a preferred embodiment of the present invention.

DETAILED DESCRIPTION OF PREFERRED EMBODIMENTS

The terms "endoscope" and "endoscopy" are used throughout in a manner somewhat broader than their customary meaning and refer to apparatus and methods which operate within body cavities, passageways and the like, such as, for example, the small intestine and the large intestine. Although these terms normally refer to visual inspection, as used herein they are not limited to applications which employ visual inspection and refer as well to apparatus, systems and methods which need not necessarily involve visual inspection.

The term "forward" refers to the remote end of an endoscope, accessory or tool furthest from the operator or to a direction facing such remote end.

The term "rearward" refers to the end portion of an endoscope, accessory or tool closest to the operator, typically outside an organ or body portion of interest or to a direction facing such end portion.

Figure 1A:
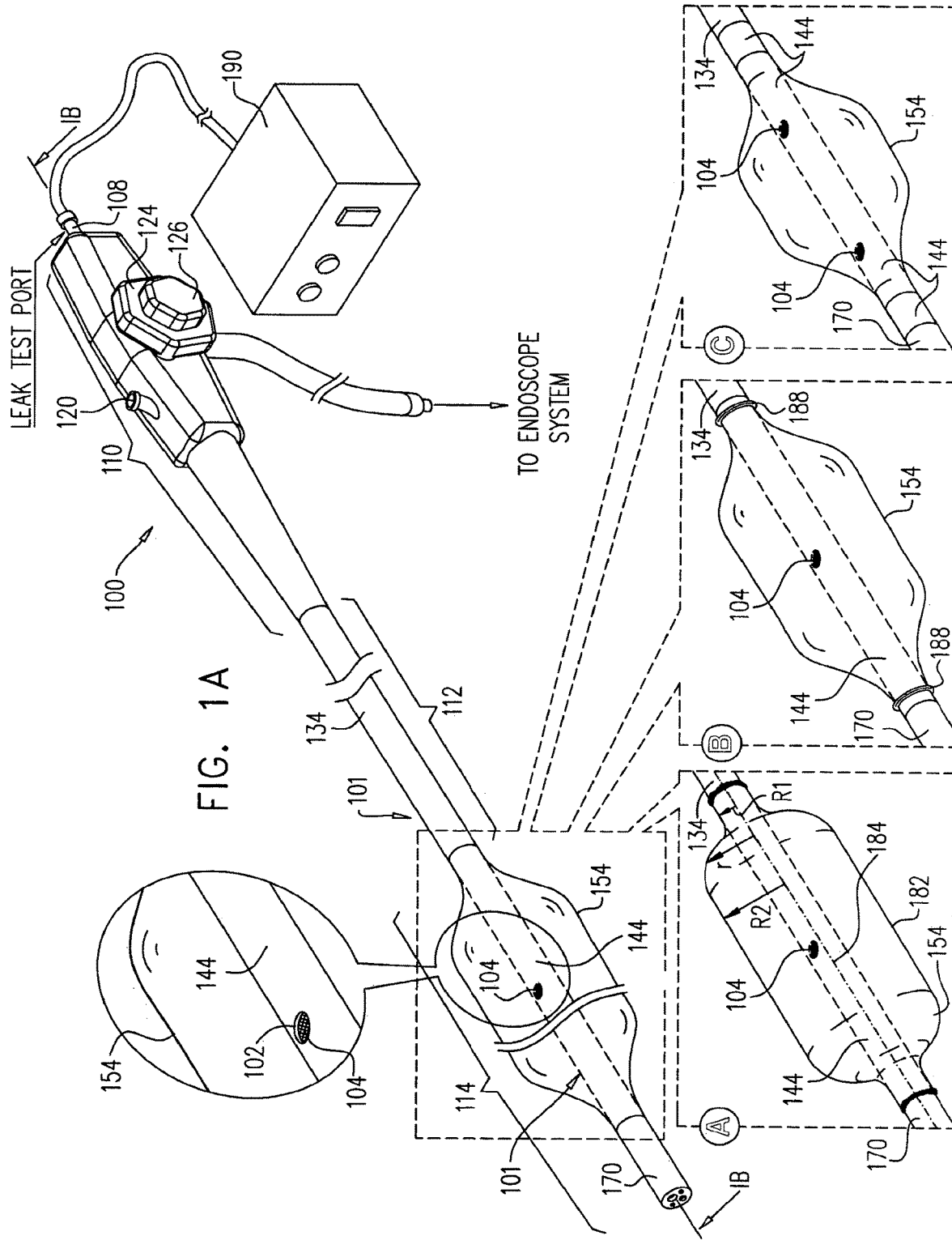
FIGS. 1A & 1B illustrate a first embodiment of a balloon endoscope constructed and operative in accordance with the present invention.
Figure 1B:
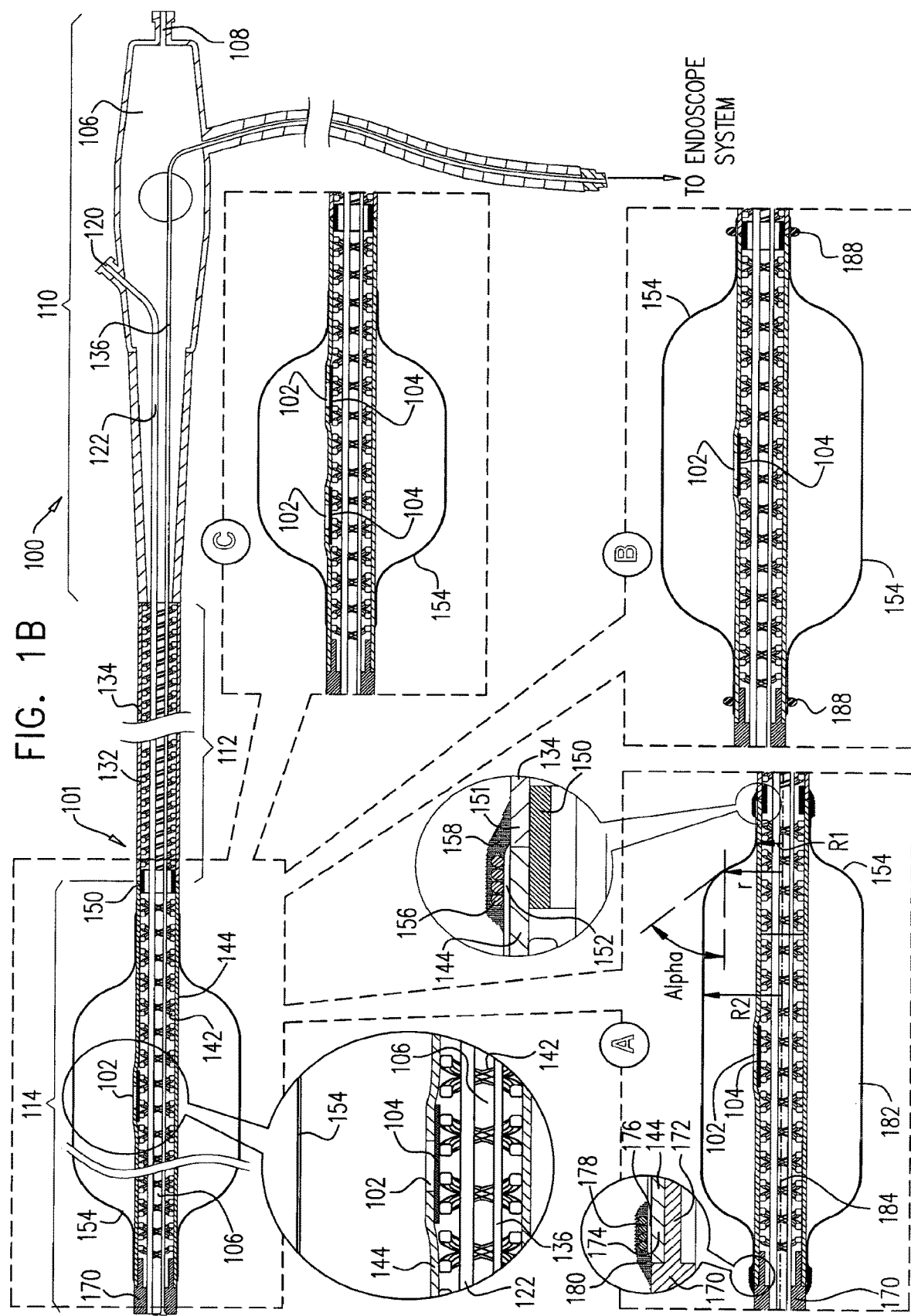

Reference is now made to FIGS. 1A & 1B, which illustrate a first embodiment of a balloon endoscope constructed and operative in accordance with the present invention. As seen in FIGS. 1A & 1B, an endoscope 100 is connected to an endoscope system (not shown). Other than as specifically described hereinbelow, the endoscope 100 may be a conventional endoscope such as an EC-3470LK video colonoscope or a VSB-3430K video enteroscope which are commercially available from Pentax Europe GmbH, 104 Julius-Vosseler St. 22527 Hamburg, Germany, and the endoscope system may be a conventional endoscope system such as a console including a EPK-1000 video processor and a SONY LMD-2140MD medical grade flat panel LCD monitor, all commercially available from Pentax Europe GmbH, 104 Julius-Vosseler St., 22527 Hamburg, Germany.

As distinct from a conventional endoscope, the endoscope 100 has an outer sheath 101 which is preferably provided with at least one balloon inflation/deflation aperture 102, with which is associated a fluid flow discriminator such as a filter 104, preferably a gas permeable, liquid impermeable filter, for example a Polytetrafluoroethylene filter, such as a Polytetrafluoroethylene filer sheath forming part of Hydrophobic Filter product P/N 28211, commercially available from Qosina Inc., 150-Q Executive Drive Edgewood, N.Y. 11717-8329 USA. Aperture 102 preferably communicates with an interior volume 106 of the endoscope 100, which in conventional endoscopes is sealed from the exterior other than via a leak test port 108 at a rearward portion 110 of the endoscope. In accordance with a preferred embodiment of the present invention, interior volume 106 generally fills the interior of the endoscope 100.

Alternatively, depending on the configuration of the endoscope, the leak test port 108 need not be located as illustrated in FIGS. 1A & 1B but may be at a different location.

Alternatively one or more aperture 102 and filter 104 may be provided in the absence of a balloon for other applications such as insufflation of a body cavity, such as an intestine, by pressurizing the interior volume 106 of the endoscope via leak test port 108 and one or more aperture 102 and filter 104.

Alternatively, as not shown, aperture 102 and filter 104 may communicate with a fluid flow passageway other than interior volume 106, such as, for example, a fluid or other conduit, such as conventional dedicated balloon inflation/deflation channels, which are not known to be associated with filters at a forward portion thereof.

As in conventional endoscopes, endoscope 100 includes, forward of rearward portion 110, an insertion tube portion 112 and, at a forward portion of endoscope 100, a bending section 114. In the embodiment of FIGS. 1A & 1B aperture 102 and filter 104 are located in the bending section 114 of endoscope 100.

Rearward portion 110 preferably includes, in addition to leak test port 108, an instrument channel port 120, which communicates with an instrument channel 122, extending throughout the length of endoscope 100. Rearward portion 110 preferably also includes conventional user interface elements, such as steering knobs 124 and 126 and other elements (not shown) and defines an interior volume, which forms part of interior volume 106 and communicates with the leak test port 108.

Insertion tube portion 112 includes a reinforcement mesh 132 which serves to maintain the interior volume thereof against collapse during bending thereof so as to maintain communication therethrough between the interior volume of the rearward portion 110 and the interior volume of the bending section 114. A tubular sealing sheath 134, typically forming part of outer sheath 101, seals the interior volume of insertion tube portion 112 from the exterior of the endoscope. In addition to the instrument channel 122, an optical fiber bundle 136 also extends through the interior volume of the insertion tube portion 112. Other conduits and other elements may also extend through this interior volume.

It is appreciated that interior volume 106 substantially fills the interior of endoscope 100 which is not occupied by conduits and other elements extending therethrough. Interior volume 106 is fluid sealed from the exterior of the endoscope 100 preferably other than via leak test port 108. Accordingly, it is a particular feature of the present invention that interior volume 106 may be used, as not previously contemplated, for inflation and deflation of an endoscope balloon.

It is further appreciated that notwithstanding the fact that various conduits may extend through the interior volume 106, their presence does not result in fluid communication between the interior volume 106 and the interior of any conduit extending therethrough.

Bending section 114 includes a selectably bendable reinforcement mesh 142 which is selectably bendable in response to operator manipulation of steering knobs 124 and 126. The interior volume of bending section 114 is thus also protected against collapse during bending thereof so as to maintain communication therethrough with the interior volumes of the insertion tube portion 112 and of the rearward portion 110. A tubular sealing bending rubber sheath 144, typically forming part of outer sheath 101, seals the interior volume of bending section 114 from the exterior of the endoscope.

Bending rubber sheath 144 may be an off-the-shelf product, such as a silicone bending rubber sheath part number SPRBSS11, PVC bending rubber sheath part number SPRBSP11, or a Viton bending rubber sheath part number SPRBSV11, all commercially available from Endoscope Repair Inc. of 5201 Blue Lagoon Drive, No. 815 Miami, Fla. 33126 USA. Instrument channel 122, optical fiber bundle 136 and optionally other elements extend through the interior volume of the bending section 114.

In accordance with a preferred embodiment of the present invention, bending section 114 includes a rigid collar element 150, preferably formed of metal, which underlies a forward end 151 of tubular sealing sheath 134 which is butted against a rearward end of sheath 144. A rearward end 152 of an inflatable tubular balloon 154 is retained over rearward end of sheath 144 preferably by a wire 156 wound thereabout. The rearward end 152 of balloon 154 is preferably additionally sealed to sheath 144 by an adhesive 158, such as a medical grade epoxy M31-CL, commercially available from Henkel Corporation, One Henkel Way Rocky Hill, Conn. 06067, USA.

Further in accordance with a preferred embodiment of the present invention, bending section 114 includes a rigid tip portion 170, preferably formed of metal or plastic, a rearward portion 172 of which underlies a forward end 174 of sheath 144. A forward end 176 of inflatable tubular balloon 154 is retained over forward end 174 of sheath 144 preferably by a wire 178 wound thereabout. The forward end 176 of balloon 154 is preferably additionally sealed to rigid tip portion 170 by an adhesive 180, such as a medical grade epoxy M31-CL, commercially available from Henkel Corporation, One Henkel Way Rocky Hill, Conn. 06067, USA.

Filter 104 is preferably connected to sheath 144 underlying aperture 102 by any suitable technique, such as the use of adhesive, for example a Polychloroprene based Contact Cement commercially available from Elmer's Products Inc. of One Easton Oval Columbus, Ohio 43219, USA, may be used. It is appreciated that a gas communication path extends between the leak test port 108 via the interior volume 106, filter 104 and aperture 102 to a balloon volume at the interior of inflatable/deflatable balloon 154.

It is a particular feature of the present invention that inflatable/deflatable balloon 154 is inflated and/or deflated via the interior volume 106 of the balloon endoscope 100. The available cross section of the interior volume 106 for inflation/deflation of the balloon 154 is typically 15-25 square millimeter, which is approximately 6-15 times greater than the cross section of balloon inflation channels employed in the prior art. This enables inflation and deflation of the balloon 154 to take place significantly faster than in prior art balloon endoscopes.

It is appreciated that the present invention enables retrofit of existing non-balloon endoscopes to become balloon endoscopes, without the complications and per treatment costs associated with conventional external balloon devices. These complications include limitations on bendability, torqueability and maneuverability as well as increased cross section and increased endoscope head resistance to advancement. Prior art balloon endoscopes have increased per treatment costs arising from difficulties in reprocessing, cleaning and disinfection thereof, resulting in single-use components, which are obviated in the operation of the present invention.

As seen in FIGS. 1A & 1B, the configuration of inflatable/deflatable balloon 154 is preferably as shown at A, characterized as follows:

Balloon 154 preferably has an overall length of 70-130 mm, more preferably 90-110 mm. Rearward and forward ends 152 and 176 respectively of balloon 154 are generally cylindrical and have a fixed inner cross-sectional radius R1, when forming part of balloon endoscope 100. R1 is preferably between 4 and 7 mm so as to tightly engage the adjacent portions of the endoscope.

A central cylindrical portion 182 of balloon 154 typically has a length of 25-70 mm and more preferably 30-55 mm and has a fixed inner cross-sectional radius R2, when inflated to a nominal pressure, such as 10-20 millibars in excess of atmospheric pressure. R2 is preferably between 20 and 35 mm depending on the application.

Extending between the central cylindrical portion 182 and each of the rearward and forward ends 152 and 176 respectively are circularly symmetric tapered portions whose inner radius changes from R2 to R1 preferably in accordance with the following function:

$$\cos(\mathrm{Alpha}) \geq r/R2$$

where r is the inner radius of the balloon at a given location between the central cylindrical portion 182 and one of ends 152 and 176; and Alpha is the angle between the tangent to the balloon at the given location and a longitudinal axis of symmetry of the balloon, here indicated by reference numeral 184.

More preferably, cos(Alpha) is approximately equal to r/R2.

It is appreciated that the foregoing balloon configuration is applicable not only to balloon endoscopes but also to balloon catheters, with suitable adjustment being made to R1 and R2.

Alternatively other balloon configurations may be employed, such as that shown at B.

As also seen in FIGS. 1A & 1B, the inflatable/deflatable balloon 154 may be fixed to the endoscope as described hereinabove and shown at A. Alternatively, the inflatable/deflatable balloon 154 may be removably attached to the endoscope as by stretchable rings 188, as shown at B.

As additionally seen in FIGS. 1A & 1B, a single aperture 102 may be provided for gas communication between the interior of inflatable/deflatable balloon 154 and the interior volume 106 of endoscope 100 as described hereinabove and shown at A and B. Alternatively, plural apertures 102, having associated therewith plural filters 104 may be provided for gas communication between the interior of inflatable/deflatable balloon 154 and the interior volume 106 of endoscope 100, as shown as C.

As further seen in FIGS. 1A & 1B, the length of balloon 154 is preferably approximately similar to the length of the bending rubber sheath 144 and aligned therewith, as shown at A and B. This alignment allows rearward end 152 of balloon 154 to be mounted over the rigid collar element 150, by the wires 156 and adhesive 158 as shown at A together with underlying rearward end of sheath 144, or by removable ring 188 as shown at B, and allows forward end 176 of balloon 154 to be mounted over the rigid rearward portion 172 of rigid tip portion 170, by wires 178 and adhesive 180 as shown at A together with underlying forward end 174 of sheath 144, or by removable ring 188 as shown at B.

Alternatively, as shown at C in FIGS. 1A & 1B, the length of balloon 154 is shorter than the length of bending rubber sheath 144, in which case end portions 152 and 176 of balloon 154 may be fixed to the bending rubber sheath 144 by any suitable known technique, such as by adhesive or by ultrasonic welding.

It is a particular feature of the present invention that an inflation/deflation control system 190 is coupled to the interior volume 106 of the endoscope 100 via leak test port 108.

Reference is now made to FIGS. 2A & 2B, which illustrate a second embodiment of a balloon endoscope constructed and operative in accordance with the present invention. As seen in FIGS. 2A & 2B, an endoscope 200 is connected to an endoscope system (not shown). Other than as specifically described hereinbelow, the endoscope 200 may be a conventional endoscope such as an EC-3470LK video colonoscope or a VSB-3430K video enteroscope which are commercially available from Pentax Europe GmbH, 104 Julius-Vosseler St. 22527 Hamburg, Germany, and the endoscope system may be a conventional endoscope system such as a console including a EPK-1000 video processor and a SONY LMD-2140MD medical grade flat panel LCD monitor, all commercially available from Pentax Europe GmbH, 104 Julius-Vosseler St., 22527 Hamburg, Germany.

An interior volume 206 of the endoscope 200, which preferably generally fills the interior of the endoscope 200, is sealed from the exterior other than via a leak test port 208 at a rearward portion 210 of the endoscope 200.

As in conventional endoscopes, endoscope 200 includes, forward of rearward portion 210, an insertion tube portion 212 and, at a forward portion of endoscope 200, a bending section 214.

Rearward portion 210 preferably includes, in addition to leak test port 208, an instrument channel port 220, which communicates with an instrument channel 222, extending throughout the length of endoscope 200. Rearward portion 210 preferably also includes conventional user interface elements, such as steering knobs 224 and 226 and other elements (not shown) and defines an interior volume, which forms part of interior volume 206 and communicates with the leak test port 208.

Insertion tube portion 212 includes a reinforcement mesh 232 which serves to maintain the interior volume thereof against collapse during bending thereof so as to maintain communication therethrough between the interior volume of the rearward portion and the interior volume of the bending section 214. A tubular sealing sheath 234 seals the interior volume of insertion tube portion 212 from the exterior of the endoscope. In addition to the instrument channel 222, an optical fiber bundle 236 also extends through the interior volume of the insertion tube portion 212. Other conduits and elements may also extend through this interior volume.

Bending section 214 includes a selectably bendable reinforcement mesh 242 which is selectably bendable in response to operator manipulation of steering knobs 224 and 226. The interior volume of bending section 214 is thus also protected against collapse during bending thereof so as to maintain communication therethrough with the interior volumes of the insertion tube portion 212 and of the rearward portion 210.

A tubular sealing bending rubber sheath 244 seals the interior volume of bending section 214 from the exterior of the endoscope. Instrument channel 222, an optical fiber bundle 236 and optionally other elements and conduits extend through the interior volume 246 of the bending section 214.

As distinct from a conventional endoscope, tubular sealing bending rubber sheath 244 includes an integrally formed selectably inflatable/deflatable balloon portion 248, the interior of which communicates with the interior volume 246 of the bending section 214. Bending rubber sheath 244 with balloon portion 248 may be made of a generally stretchable material such as silicon, or a relatively non-stretchable material such as PVC, polyurethane, nylon or other polymeric material.

In accordance with a preferred embodiment of the present invention, bending section 214 includes a rigid collar element 250, preferably formed of metal, which underlies a forward end 251 of tubular sealing sheath 234 which is butted against a rearward end of sheath 244.

A fluid flow discriminator such as an in-line filter 252, preferably a gas permeable, liquid impermeable filter, for example a Polytetrafluoroethylene filer, such as a Polytetrafluoroethylene filer sheath forming part of Hydrophobic Filter product P/N 28211, commercially available from Qosina Inc., 150-Q Executive Drive Edgewood, N.Y. 11717-8329 USA, is disposed within rigid collar element 250 and prevents liquid from passing between the interior volume 246 of the bending section 214 and the interior volume 206 of the remainder of the endoscope rearwardly thereof. It is appreciated that a gas communication path extends between the leak test port 208 via the interior volume 206, filter 252 and interior volume 246 to the interior of inflatable/deflatable balloon portion 248.

Alternatively, as not shown, the interior of integrally formed balloon portion 248 and filter 252 may communicate with a fluid flow passageway other than interior volume 206, such as, for example, a fluid or other conduit, such as conventional dedicated balloon inflation/deflation channels, which are not known to be associated with filters at a forward portion thereof.

A rearward end 253 of tubular sealing bending rubber sheath 244 is retained over rigid collar element 250 preferably by a wire 256 wound thereabout. The rearward end 253 of tubular sealing bending rubber sheath 244 is preferably additionally sealed to sheath 234 by an adhesive 258, such as a medical grade epoxy M31-CL, commercially available from Henkel Corporation, One Henkel Way Rocky Hill, Conn. 06067, USA.

Further in accordance with a preferred embodiment of the present invention, bending section 214 includes a rigid tip portion 270, preferably formed of metal or plastic, a rearward portion 272 of which underlies a forward end 274 of sheath 244. Forward end 274 of sheath 244 is retained over rearward portion 272 of rigid tip portion 270 preferably by a wire 278 wound thereabout. The forward end 274 of sheath 244 is preferably additionally sealed to rigid tip portion 270 by an adhesive 280, such as a medical grade epoxy M31-CL, commercially available from Henkel Corporation, One Henkel Way Rocky Hill, Conn. 06067, USA.

It is a particular feature of the present invention that an inflation/deflation control system 290 is coupled to the interior volume 206 of the endoscope 200 via leak test port 208.

Figure 3A:
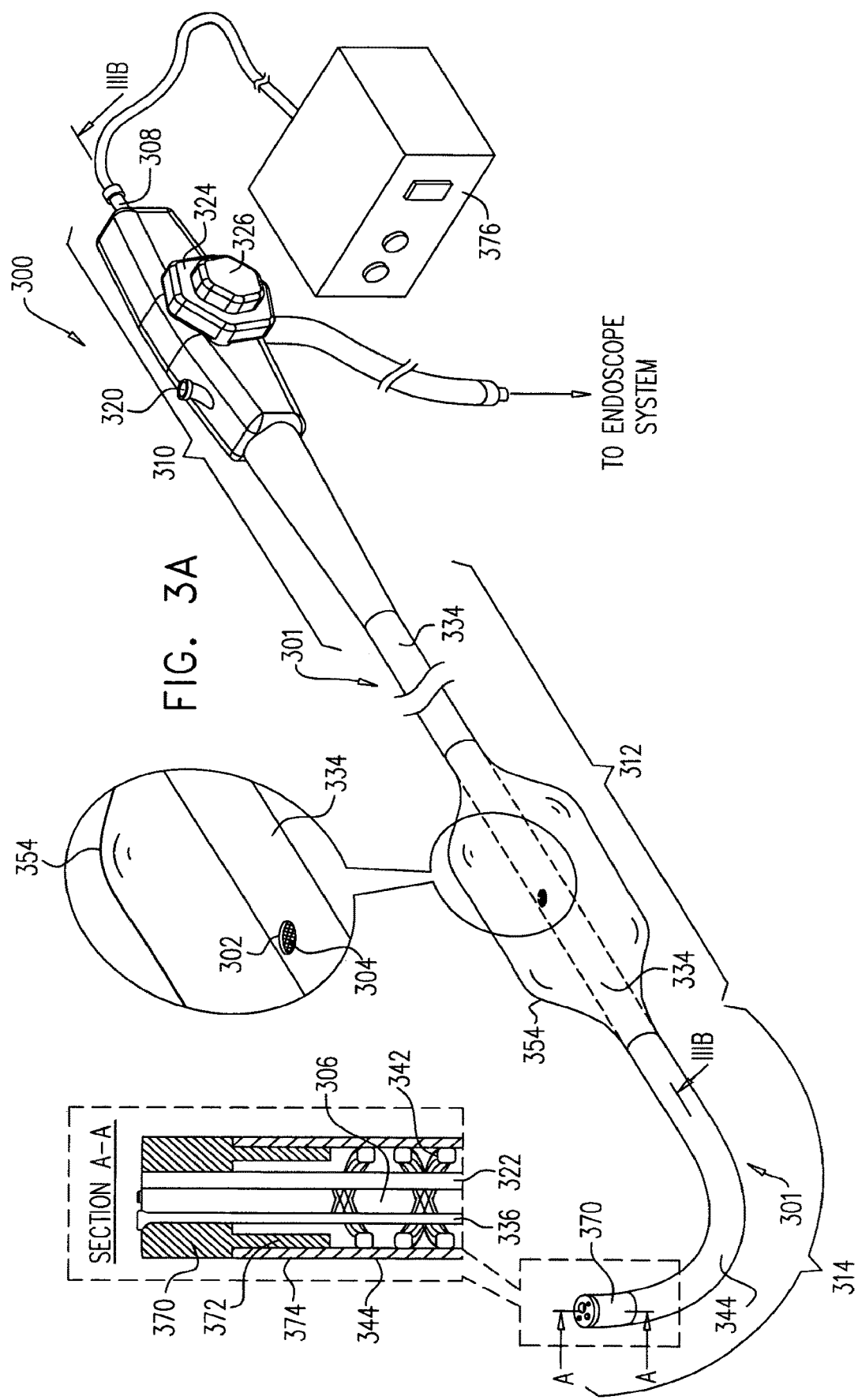

Reference is now made to FIGS. 3A & 3B, which illustrate a third embodiment of a balloon endoscope constructed and operative in accordance with the present invention. As seen in FIGS. 3A & 3B, an endoscope 300 is connected to an endoscope system (not shown). Other than as specifically described hereinbelow, the endoscope 300 may be a conventional endoscope such as an EC-3470LK video colonoscope or a VSB-3430K video enteroscope which are commercially available from Pentax Europe GmbH, 104 Julius-Vosseler St. 22527 Hamburg, Germany, and the endoscope system may be a conventional endoscope system such as a console including a EPK-1000 video processor and a SONY LMD-2140MD medical grade flat panel LCD monitor, all commercially available from Pentax Europe GmbH, 104 Julius-Vosseler St., 22527 Hamburg, Germany.

As distinct from a conventional endoscope, the endoscope 300 preferably includes an outer sheath 301 which is preferably provided with at least one balloon inflation/deflation aperture 302, with which is associated a fluid flow discriminator such as a filter 304, preferably a gas permeable, liquid impermeable filter, for example a Polytetrafluoroethylene filer, such as a Polytetrafluoroethylene filer sheath forming part of Hydrophobic Filter product P/N 28211, commercially available from Qosina Inc., 150-Q Executive Drive Edgewood, N.Y. 11717-8329 USA. Aperture 302 communicates with an interior volume 306 of the endoscope, which in conventional endoscopes is sealed from the exterior other than via a leak test port 308 at a rearward portion 310 of the endoscope.

Alternatively, as not shown, aperture 302 and filter 304 may communicate with a fluid flow passageway other than interior volume 306, such as, for example, a fluid or other conduit, such as conventional dedicated balloon inflation/deflation channels, which are not known to be associated with filters at a forward portion thereof.

In accordance with a preferred embodiment of the present invention, interior volume 306 generally fills the interior of the endoscope 300.

As in conventional endoscopes, endoscope 300 includes, forward of rearward portion 310, an insertion tube portion 312 and, at a forward portion of endoscope 300, a bending section 314. Aperture 302 and filter 304 are located in the insertion tube portion 312 of endoscope 300.

Rearward portion 310 preferably includes, in addition to leak test port 308, an instrument channel port 320, which communicates with an instrument channel 322, extending throughout the length of endoscope 300. Rearward portion 310 preferably also includes conventional user interface elements, such as steering knobs 324 and 326 and other elements (not shown) and defines an interior volume, which forms part of interior volume 306 and communicates with the leak test port 308.

Insertion tube portion 312 includes a reinforcement mesh 332 which serves to maintain the interior volume thereof against collapse during bending thereof so as to maintain communication therethrough between the interior volume of the rearward portion and the interior volume of the bending section 314. A tubular sealing sheath 334, typically forming part of outer sheath 301, seals the interior volume of insertion tube portion 312 from the exterior of the endoscope. In addition to the instrument channel 322, an optical fiber bundle 336 also extends through the interior volume of the insertion tube portion 312. Other conduits and elements may also extend through this interior volume.

Bending section 314 includes a selectably bendable reinforcement mesh 342 which is selectably bendable in response to operator manipulation of steering knobs 324 and 326. The interior volume of bending section 314 is thus also protected against collapse during bending thereof so as to maintain communication therethrough with the interior volumes of the insertion tube portion 312 and of the rearward portion 310. A tubular sealing bending rubber sheath 344, typically forming part of outer sheath 301, seals the interior volume of bending section 314 from the exterior of the endoscope. Bending rubber sheath 144 may be an off-the-shelf product, such as a silicone bending rubber sheath part number SPRBSS11, PVC bending rubber sheath part number SPRBSP11, or a Viton bending rubber sheath part number SPRBSV11, all commercially available from Endoscope Repair Inc. of 5201 Blue Lagoon Drive, No. 815 Miami, Fla. 33126 USA.

Instrument channel 322, an optical fiber bundle 336 and optionally other conduits and elements extend through the interior volume of the bending section 314.

In accordance with a preferred embodiment of the present invention, bending section 314 includes a rigid collar element 350, preferably formed of metal, which underlies a forward end 351 of tubular sealing sheath 334 which is butted against a rearward end of sheath 344.

An inflatable tubular balloon 354 is sealingly mounted over tubular sealing sheath 334 of insertion tube portion 312, overlying aperture 302 and filter 304 as by any suitable technique such as ultrasonic welding or an adhesive 358.

Further in accordance with a preferred embodiment of the present invention, bending section 314 includes a rigid tip portion 370, preferably formed of metal or plastic, a rearward portion 372 of which underlies a forward end 374 of sheath 344.

Filter 304 is preferably connected to sheath 334 underlying aperture 302 by any suitable technique, such as the use of adhesive. It is appreciated that a gas communication path extends between the leak test port 308 via the interior volume 306, filter 304 and aperture 302 to the interior of inflatable/deflatable balloon 354.

It is a particular feature of the present invention that an inflation/deflation control system 376 is coupled to the interior volume 306 of the endoscope 300 via leak test port 308.

Figure 4:
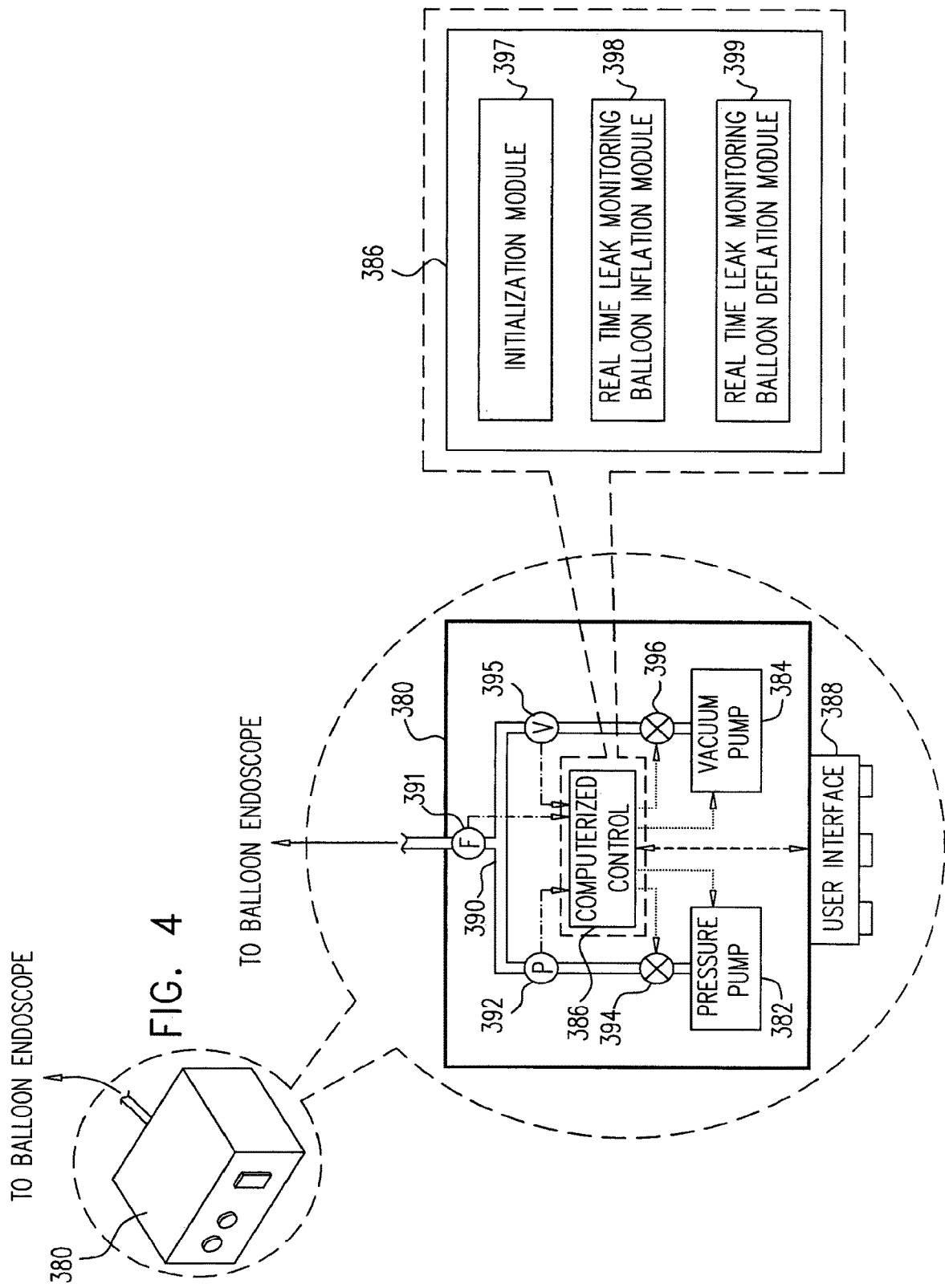
FIG. 4 is a simplified illustration of an inflation/deflation control system preferably forming part of the balloon endoscopes of FIGS. 1A-3B.

Reference is now made to FIG. 4, which is a simplified illustration of an inflation/deflation control system 380 useful in the balloon endoscopes of FIGS. 1A-3B.

As seen in FIG. 4, the inflation/deflation control system 380 preferably includes a pressure pump 382 and a vacuum pump 384, which are preferably at least partially controlled by a computerized control sub-system 386 having associated therewith a user interface 388, preferably including buttons and visually sensible indicators. Preferably pressure pump 382 and vacuum pump 384 are each connectable to a leak test port of a balloon endoscope, such as that shown in FIGS. 1A-3B (not shown in FIG. 4) via a manifold 390 and a flow meter 391. A pressure sensor 392 and a pressure valve 394 are preferably connected in series between the pressure pump 382 and manifold 390. A vacuum sensor 395 and a vacuum valve 396 are preferably connected in series between the vacuum pump 384 and manifold 390.

The computerized control sub-system 386 preferably includes initialization module 397, preferably operative prior to insertion of the balloon endoscope into a body cavity; and a real time leak monitoring balloon inflation module 398 and a real time leak monitoring balloon deflation module 399, both preferably operative when the balloon endoscope is inserted at a desired location in a body cavity.

The initialization module 397, which is preferably automatically operated upon turning on the inflation/deflation control system 380 preferably has the following functionality:
  balloon endoscope pressurization producing balloon inflation;
  pressure leak test when balloon endoscope is in a pressurized state and the balloon is surrounded by a balloon confining, gas permeable collar member;
  balloon endoscope depressurization producing balloon deflation;
  vacuum leak test when balloon endoscope is in a depressurized state; and
  provision of system go/no go indication to the operator.

The real time leak monitoring balloon inflation module 398, which is preferably actuated by the operator following insertion of the balloon endoscope to a desired location within a body cavity, preferably has the following functionality:
  balloon endoscope pressurization producing balloon inflation;
  provision of complete balloon inflation indication to the operator;
  periodical positive pressure leak test when balloon endoscope is in a pressurized state within a body cavity such as the intestine; and
  provision of leak indication to the operator.

The real time leak monitoring balloon deflation module 399, which is preferably actuated by the operator following insertion of the balloon endoscope to a desired location within a body cavity, preferably has the following functionality:
  balloon endoscope depressurization producing balloon deflation;
  provision of complete balloon deflation indication to the operator;
  periodical negative pressure leak test when balloon endoscope is in a depressurized state within a body cavity such as the intestine; and
  provision of leak indication to the operator.

It is a particular feature of the present invention that the real time leak monitoring balloon inflation module 398 is responsive to an output from the flow meter 391 in order to distinguish between a sensed pressure drop at the interior of the endoscope which results from a change in the effective volume of the intestine during a procedure and a sensed pressure drop at the interior of the endoscope which results from a leak. By monitoring the total flow to the interior of the balloon endoscope and noting the total volume of the inflated balloon and the interior of the endoscope, a sensed pressure drop combined with an indication of fluid flow which exceeds this total volume indicates the presence of a leak.

It is appreciated that the functionality of modules 398 and 399 has utility even in the absence of a balloon, where the interior of the endoscope is sealed from the exterior thereof during operation thereof, such as in otherwise conventional endoscopes wherein automatic real time leak testing of the interior volume of the endoscope during operation of the endoscope is highly desirable.

Reference is now made to FIGS. 5A-5J, which are together a simplified pictorial flowchart which illustrates operation of a balloon endoscope in accordance with a preferred embodiment of the present invention.

Figure 5G:
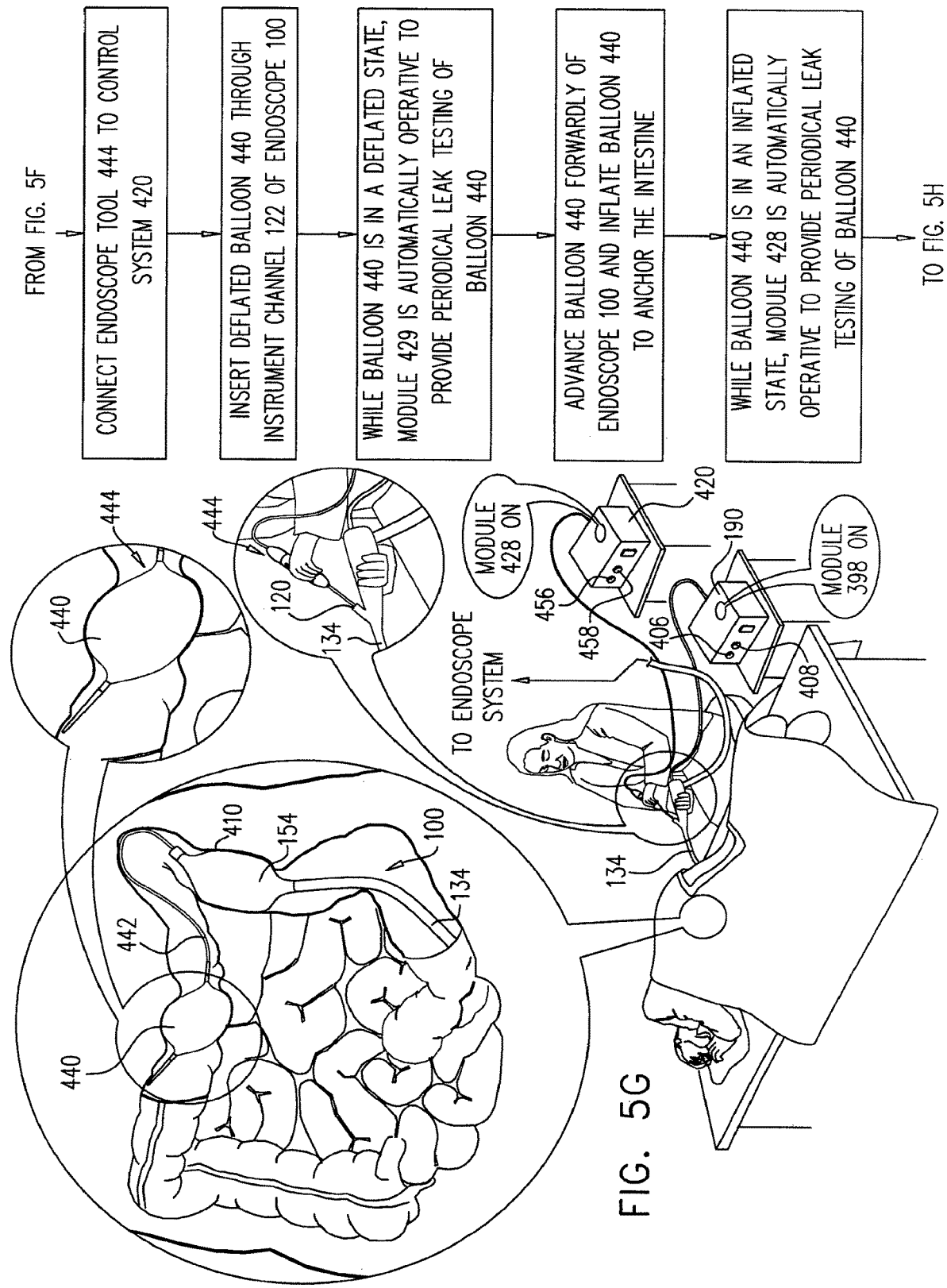

As seen in FIG. 5A, there is provided a balloon endoscope constructed and operative in accordance with a preferred embodiment of the invention, such as any one of the embodiments of an endoscope described hereinabove, and in particular for the illustrated example of FIGS. 5A-5J, the endoscope shown at A in FIGS. 1A & 1B. For the sake of convenience and conciseness, the reference numerals used in conjunction with FIGS. 1A & 1B are employed throughout the description of FIGS. 5A-5J.

Preferably prior to beginning endoscopy treatments each day, a manual leak test is performed on the endoscope 100 using a conventional endoscope leak tester 402, such as a model PLT-5500, commercially available from Instrument Specialists Inc., 32390 1H-10 West, Boerne, Tex. 78006-9214, USA, and a balloon confining, gas permeable collar member 404 which allows gas to escape from a leaky balloon but limits expansion thereof.

As seen in FIG. 5B, the leak tester 402 is operatively connected to the leak test port 108 of the balloon endoscope 100 and the collar 404 is placed over the balloon 154 of the balloon endoscope 100. Using the leak tester 402, positive pressure is applied via the test port 108 and the interior volume 106 of the balloon endoscope 100 in order to pressurize and inflate the balloon 154. The pressure within the interior volume 106 is visually monitored to detect any pressure decrease over time which would indicate a rupture in the balloon 154 or elsewhere in the endoscope 100 which would permit fluid communication between the exterior of the endoscope 100 and its interior volume 106.

Upon successful completion of the leak test, the leak tester 402 and the collar 404 are detached from the endoscope 100, which is ready for clinical use.

Reference is now made to FIG. 5C, which illustrates a novel further leak test performed in a clinical setting just prior to insertion of the endoscope 100 into a body cavity. As indicated in FIG. 5C, collar 404 is placed over balloon 154 and inflation/deflation control system 190 is coupled to the interior volume 106 of the endoscope 100 via leak test port 108. The operator initiates an automatic Clinical Integrity Test Protocol (CITP) preferably by actuating a CITP button 406.

The Clinical Integrity Test Protocol preferably includes, inter alia, (a) a leak test during balloon inflation and (b) a subsequent leak test during application of vacuum to the balloon. Preferably, upon successful completion of the Clinical Integrity Test Protocol, a visual indication is automatically provided to the operator, such as by illumination of an indicator light 408.

Immediately following successful completion of the CITP protocol, as shown in FIG. 5D, the endoscope 100 may be inserted, with balloon 154 in a deflated state, into a body cavity, such as a patient's intestine and advanced to a location 410 therein at which it is desired to inflate balloon 154.

While balloon 154 is still in a deflated state, module 399 is automatically operative to provide periodic leak testing of balloon 154 and the interior volume 106 of endoscope 100, while the endoscope is in a body cavity.

The balloon 154 is then inflated at location 410, as shown in FIG. 5E by supplying pressurized gas via the leak test port 108 and the interior volume 106 of the endoscope 100 to the interior of the balloon 154. While balloon 154 is in an inflated state, module 398 is automatically operative to provide periodic leak testing of balloon 154 and the interior volume 106 of endoscope 100, while the endoscope is in a body cavity.

Inflation of balloon 154 is preferably operative to anchor the balloon endoscope and thereby to spatially stabilize the endoscope 100 in the intestine and allow various diagnostic and/or therapeutic procedures to be carried out using conventional endoscope tools and techniques as indicated, for example in FIG. 5F. Examples of diagnostic and/or therapeutic procedures which are advantageously carried out using the balloon endoscope 100 include removal of polyps, as shown in FIG. 5F, performing biopsies, dilating strictures, suturing, stapling and clipping. Following completion of the diagnostic and/or therapeutic procedures, the endoscope tools may be removed and the balloon 154 may be deflated to allow advancement or retraction of the endoscope.

A two-balloon technique, such as that illustrated in FIGS. 5G & 5H may be employed in order to facilitate advancement of the balloon endoscope in the intestine. Conventional two-balloon endoscope advancement is known, and described in details for example in applicant's copending PCT Application No. PCT/IL2005/000152, filed Feb. 7, 2005; PCT Application No. PCT/IL2005/000849, filed Aug. 8, 2005; PCT Application No. PCT/IL2007/000600, filed May 17, 2007; and in US patent application publication No. US 2005/0171400. FIGS. 5G & 5H show the provision of a second inflation/deflation control system 420, which may be identical in structure and function to inflation/deflation control system 380 (FIG. 4) and is also useful with the balloon endoscopes of FIGS. 1A-3B.

Second inflation/deflation control system 420 preferably includes an initialization module (not shown), similar or identical to initialization module 397 of inflation/deflation control system 380, preferably operative prior to insertion of the balloon endoscope into a body cavity. Second inflation/deflation control system 420 preferably also includes a real time leak monitoring balloon inflation module 428, similar or identical to real time leak monitoring balloon inflation module 398 of inflation/deflation control system 380 and a real time leak monitoring balloon deflation module 429, similar or identical to real time leak monitoring balloon deflation module 399, of inflation/deflation control system 380.

Second inflation/deflation control system 420 preferably communicates with an endoscope tool balloon 440 mounted on a flexible tube 442 of an endoscope tool 444. In two-balloon endoscope advancement, endoscope tool balloon 440 is operated preferably using the protocol described above with reference to FIGS. 4 and 5C. More specifically, a novel further leak test is performed in a clinical setting just prior to insertion of the endoscope tool 444 into instrument channel 122 of endoscope 100.

The operator initiates an automatic Clinical Integrity Test Protocol (CITP) preferably by actuating a CITP button 456.

The Clinical Integrity Test Protocol preferably includes, inter alia, (a) a leak test during balloon inflation and (b) a subsequent leak test during application of vacuum to the balloon. Preferably, upon successful completion of the Clinical Integrity Test Protocol, a visual indication is automatically provided to the operator, such as by illumination of an indicator light 458.

Immediately following successful completion of the CITP protocol, the endoscope tool 444 may be inserted through the instrument channel 122 in a deflated state and thereafter inflated forward of the endoscope 100, as shown in FIG. 5G.

While balloon 440 is still in a deflated state, module 429 is automatically operative to provide periodic leak testing of balloon 440 while the endoscope is in a body cavity.

While balloon 440 is an inflated state, as shown in FIG. 5G, module 428 is automatically operative to provide periodic leak testing of balloon 440, while the endoscope 100 and the balloon 440 are in a body cavity.

It is appreciated that while balloon 154 and endoscope 100 are in the body cavity, periodic leak testing thereof continues in accordance with the protocols established by modules 398 and 399, described above.

Stages of two-balloon advancement of the endoscope 100 are illustrated in FIGS. 5G and 5H, employing balloons 154 and 440. Thereafter, additional two-balloon advancement steps may take place. Following each advancement step, balloon 440 may be deflated as shown in FIG. 5H. While balloon 440 is still in a deflated state, module 429 is automatically operative to provide periodic leak testing of balloon 440. Once tool 444 is no longer required, it may be removed via the instrument channel 122, when balloon 440 is in a deflated state.

FIG. 5I shows removal of the balloon endoscope 100 from the patient body cavity, with balloon 154 in a deflated state. While balloon 154 is still in a deflated state, module 399 is automatically operative to provide periodic leak testing of balloon 154 and the interior volume 106 of endoscope 100, while the endoscope is in a body cavity.

FIG. 5J illustrates reprocessing, including cleaning of the balloon endoscope 100 following use thereof. Manual cleaning of balloon 154 while inflated is shown at A and machine cleaning of the balloon 154 within a liquid spray permeable inflation limiting collar 460 is shown at B. In both cases, the balloon 154 is preferably inflated via leak test port 108 and then sealed in an inflated state for cleaning, as by a stopcock 462.

Reference is now made to FIGS. 6A-6J, which are simplified pictorial illustrations of a method of manufacture of a balloon endoscope in accordance with a preferred embodiment of the present invention.

A conventional non-balloon endoscope 500 such as an EC-3470LK video colonoscope or a VSB-3430K video enteroscope which are commercially available from Pentax Europe GmbH, 104 Julius-Vosseler St. 22527 Hamburg, Germany, may be provided.

Alternatively, an endoscope of a different manufacturer may be employed. In such a case, a leak test port may be located at various locations or may not be provided. In the former case, if the location of the leak test port is not suitable, the existing leak test port may be sealed and a new leak test port formed, as by a retrofit procedure, at a suitable location in communication with the interior volume of the endoscope. In the latter case, a leak test port may be provided in communication with the interior volume of the endoscope, as by a retrofit procedure.

Figure 6A:
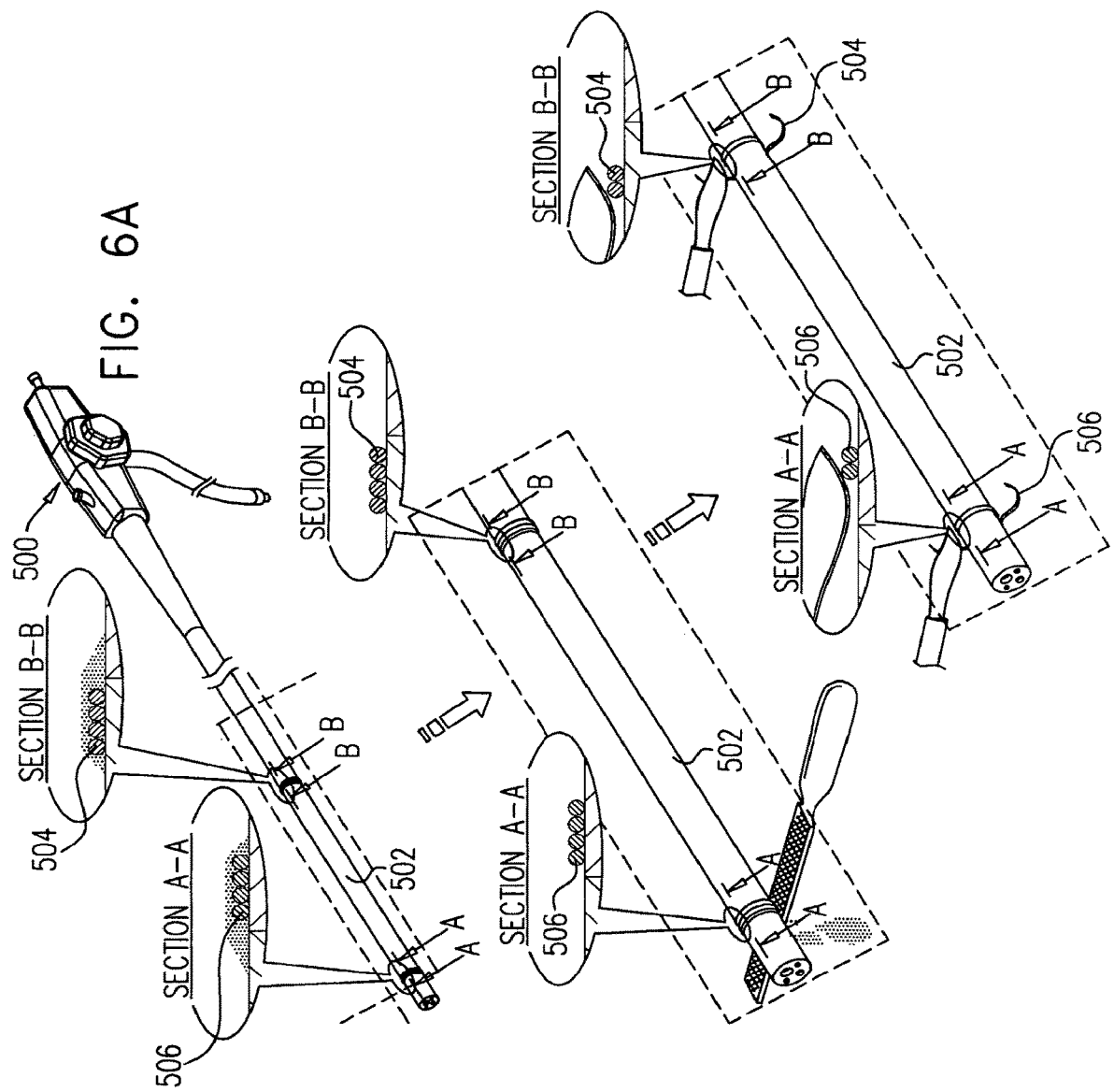
Figure 6C:
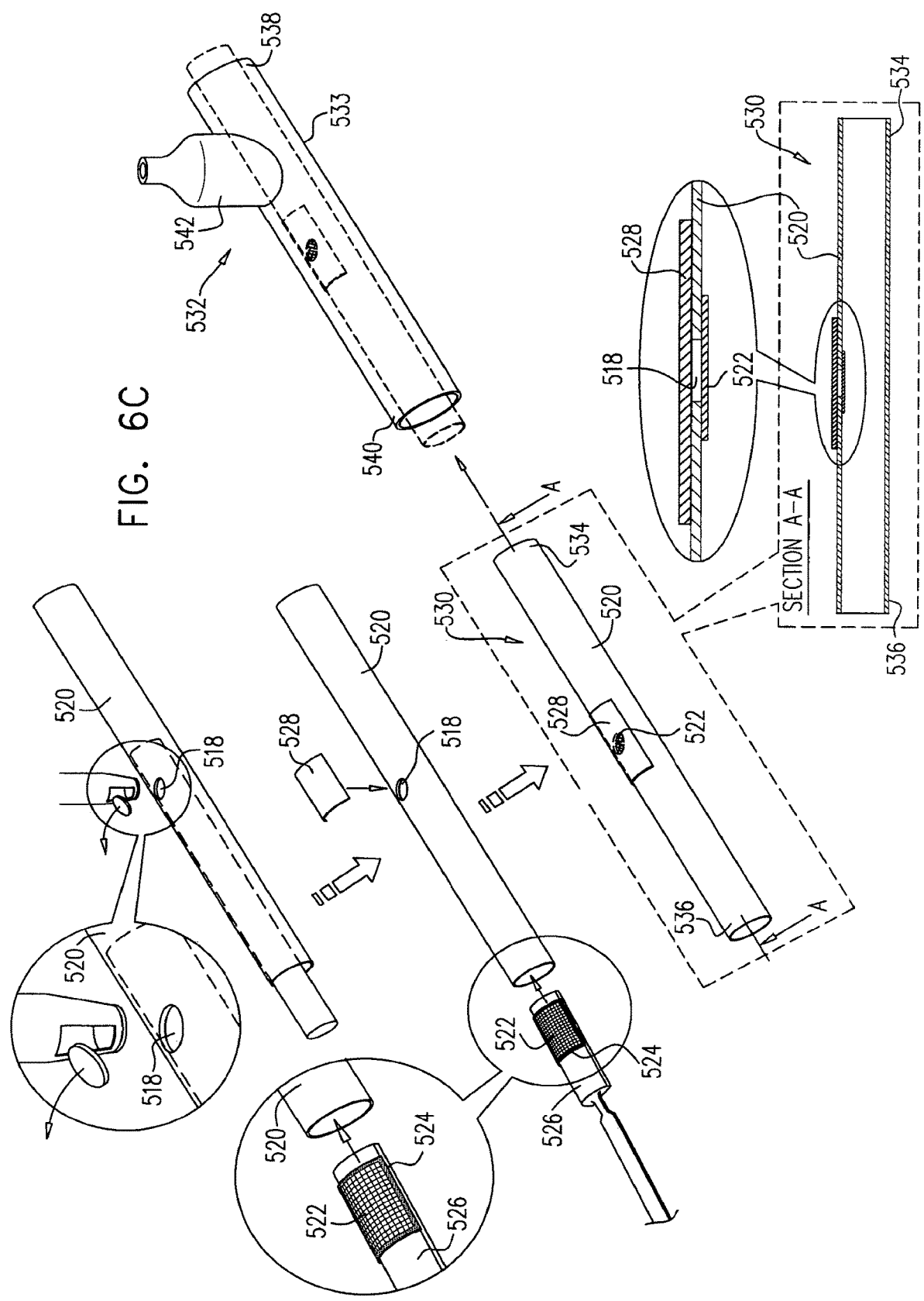

The endoscope 500 may be retrofitted as a balloon endoscope by initially removing a bending rubber sheath 502 therefrom, as seen in FIGS. 6A & 6B. This is preferably accomplished by first removing the epoxy-covered wound retaining wires 504 and 506 which attach the sheath 502 to the remainder of the endoscope 500. As shown in a simplified manner in FIG. 6A, this may be achieved by first grinding down the epoxy and then cutting the wire using a scalpel.

Thereafter, as shown in a simplified manner in FIG. 6B, the bending rubber sheath 502 may then be slit using the scalpel and an underlying protective plate inserted between the bending rubber sheath 502 and the protective mesh 508 of the endoscope 500.

The result of the steps shown in FIGS. 6A and 6B is an endoscope having an exposed bending section 510. Alternatively, an endoscope may be initially constructed to have an exposed bending section 510.

In a separate manufacturing sequence, an aperture 518 is formed in a conventional bending rubber sheath 520, such as a silicone bending rubber sheath part number SPRBSS11, PVC bending rubber sheath part number SPRBSP11, or a Viton bending rubber sheath part number SPRBSV11, all commercially available from Endoscope Repair Inc. of 5201 Blue Lagoon Drive, No. 815 Miami, Fla. 33126 USA, by any suitable technique, such as punching. A filter element 522 is preferably adhered by an adhesive 524, such as a Polychloroprene based Contact Cement commercially available from Elmer's Products Inc. of One Easton Oval Columbus, Ohio 43219, USA, to the interior of the bending rubber sheath 520 underlying aperture 518, such as by the use of an inserter 526. A removable fluid sealing patch 528 is preferably placed over the aperture 518 on the outside of the bending rubber sheath 520.

The resulting apertured, filter-equipped and sealed bending rubber sheath assembly 530 is preferably inserted into a bending rubber sheath placement tool 532. Tool 532 preferably includes a cylinder 533 which is shorter than sheath assembly 530. The axial ends 534 and 536 of sheath assembly 530 are preferably bent over onto the corresponding axial ends 538 and 540 of tool 532, as shown in FIG. 6D.

A vacuum port 542 communicates with the interior of the cylinder 533 of tool 532. A vacuum is applied between the interior of tool 532 and the exterior of sheath assembly 530 via vacuum port 542, thereby producing radial stretching of sheath assembly 530 and resulting axial expansion thereof, as shown in FIG. 6D.

Figure 6E:
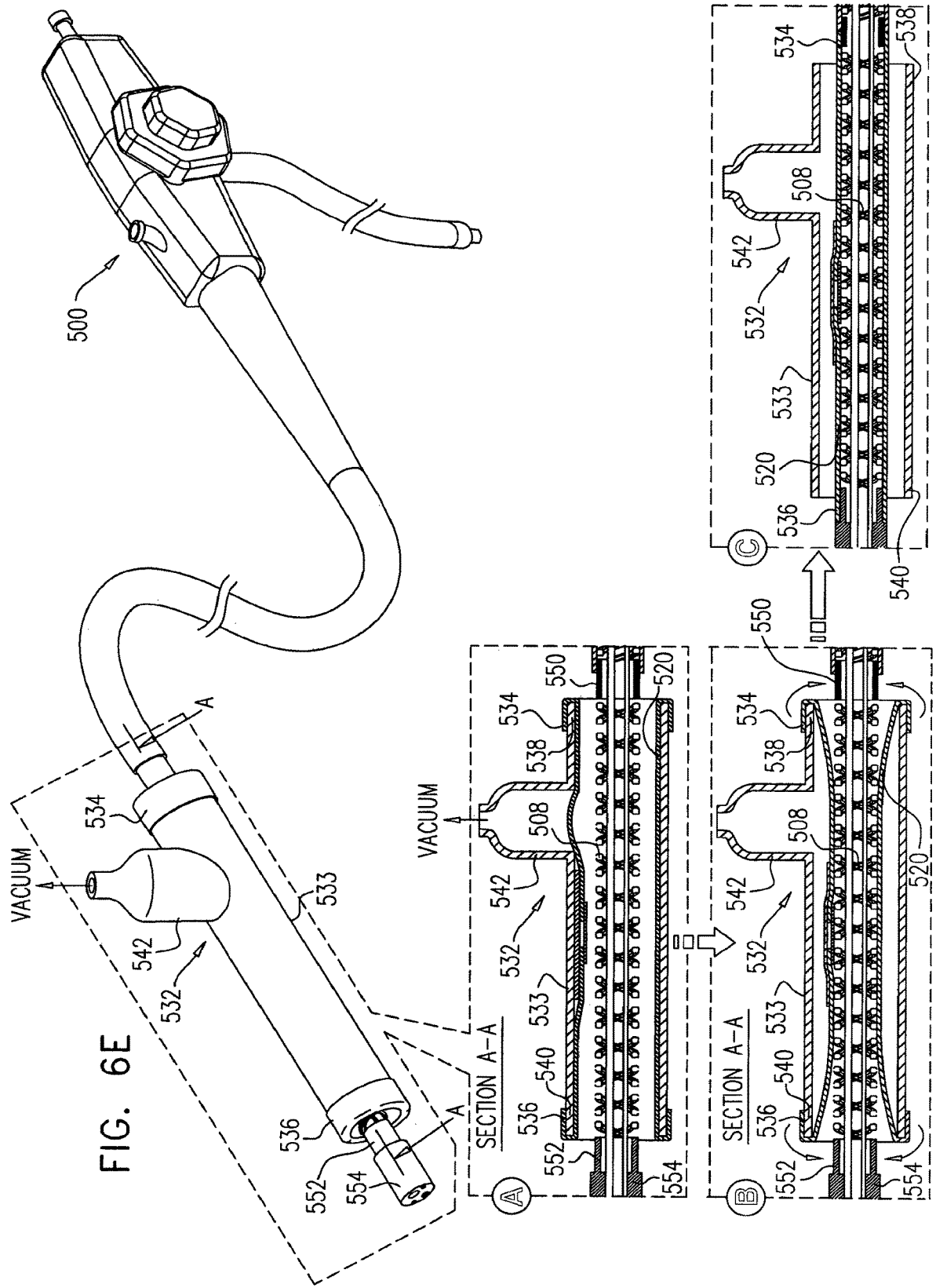

Turning now to FIG. 6E, it is seen that the endoscope having an exposed bending section 510, (FIG. 6B) is inserted into the tool 532 holding the sheath assembly 530 under vacuum in a radially expanded state (FIG. 6D), such that the rearward end 538 of tool 532 overlies a rigid collar element 550 of endoscope 500 and the forward end 540 of tool 532 overlies a rearward portion 552 of a rigid tip portion 554 of endoscope 500 as seen at A.

The vacuum is then released as shown at B, allowing part of the bending rubber assembly 530 to collapse onto the reinforcement mesh 508. As shown at C, the ends 534 and 536 of the bending rubber assembly 530 are then rolled off corresponding ends 538 and 540 of tool 532 and onto rigid collar element 550 and onto rearward portion 552 of rigid tip portion 554 of endoscope 500, respectively. As shown in FIG. 6F, the resulting partially retrofitted endoscope 560 has rearwardly facing edge 564 of bending rubber assembly 530 in butting relationship with a corresponding forwardly facing edge 566 of a tubular sealing sheath 568 of endoscope 560 as seen at A and a forwardly facing edge 570 of bending rubber assembly 530 in butting relationship with a corresponding rearwardly facing edge 572 of rigid tip portion 554 of endoscope 560, as shown at B.

As further seen in FIG. 6F, the tool 532 is slipped off of the endoscope 500 and the patch 528 is removed.

Turning to FIG. 6G, it is seen that a balloon, preferably a pre-shaped balloon 580 such as balloon 154 as described hereinabove, is slipped over the bending rubber assembly 530 of endoscope 500 such that the respective axial ends 582 and 584 of balloon 580 are aligned with respective ends 534 and 536 of the bending rubber assembly 530 and more particularly preferably such that a rearwardly facing edge 588 of balloon 580 overlies rearwardly facing edge 564 of bending rubber assembly 530 and a forwardly facing edge 590 of balloon 580 overlies forwardly facing edge 570 of bending rubber assembly 530.

Figure 6H:
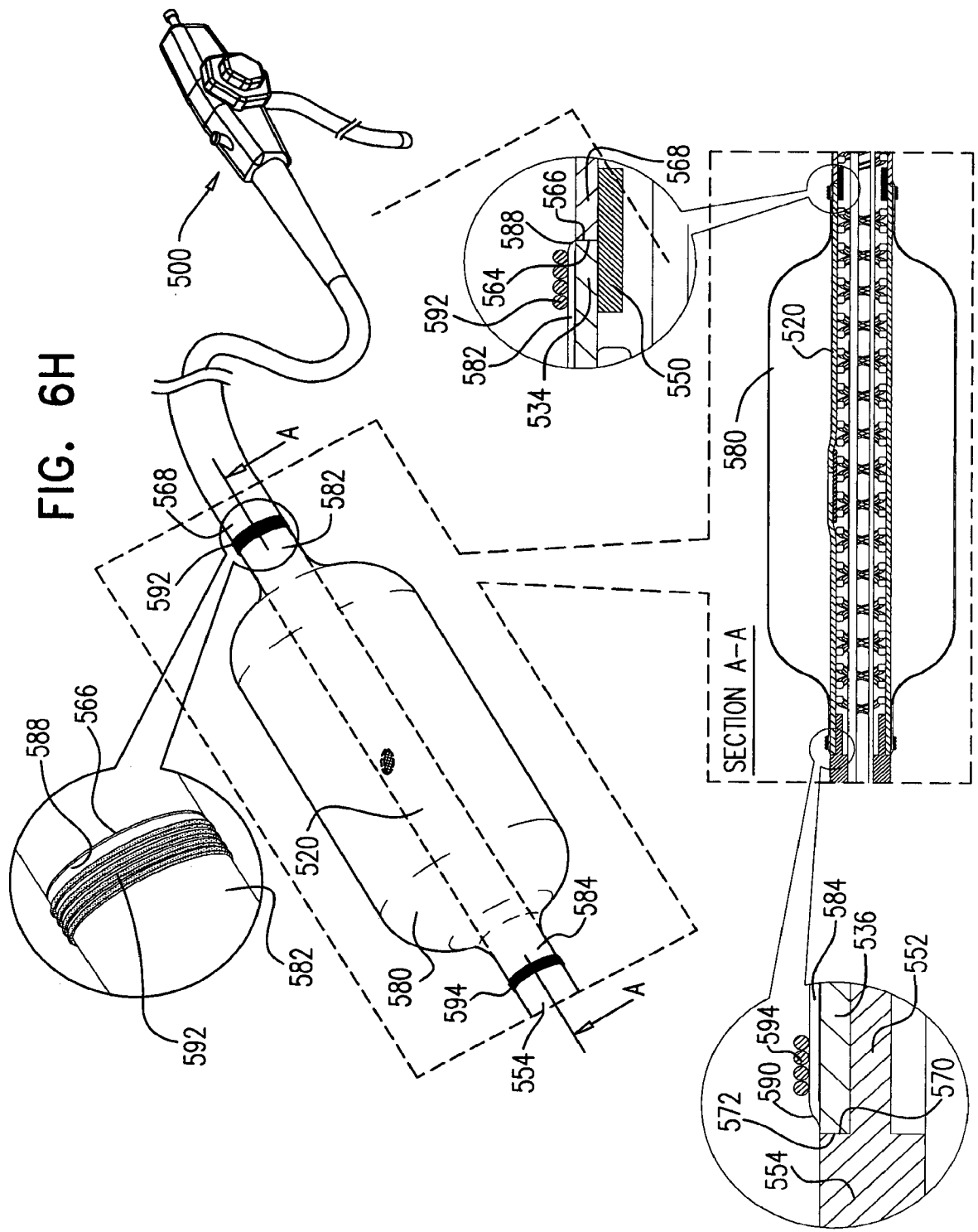
Figure 61:
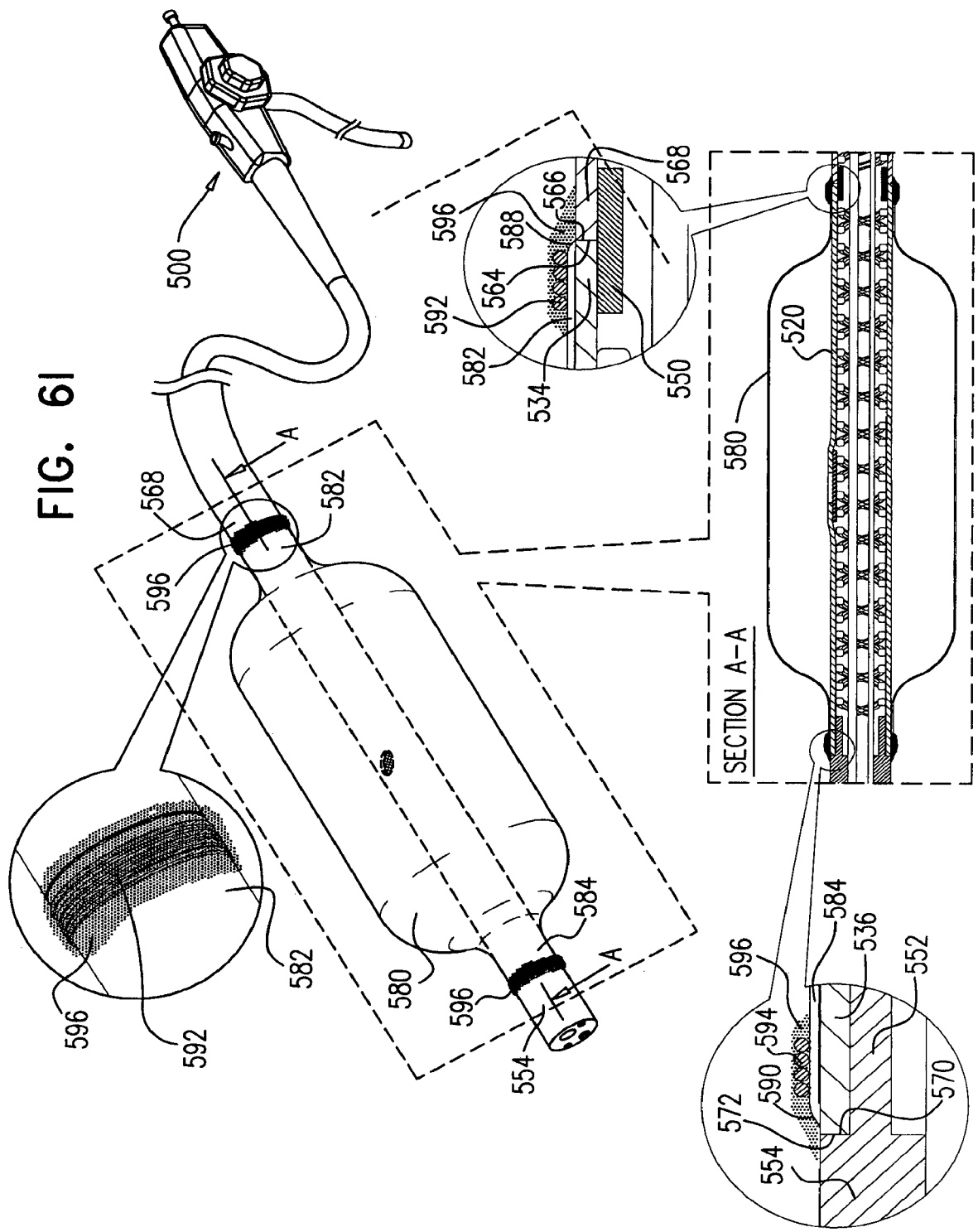

As seen in FIG. 6H, wires 592 and 594 are tightly wound about respective ends 582 and 584 of balloon 580. Thereafter, as seen in FIG. 6I, the wound wires are preferably encased in epoxy 596 together with the respective butting edges 564 & 566 and 570 & 572 and corresponding ends 534 and 536 of bending rubber assembly 530.

The steps shown particularly in FIGS. 6H and 6I provide fluid sealing between the interior volume of the balloon 580 and the exterior thereof and also provides fluid sealing between respective ends 534 and 536 of the bending rubber assembly 530 and rigid collar element 550 and rearward portion 552 of rigid tip portion 554 of endoscope 500. The provision of epoxy 596 additionally provides fluid sealing between the respective butting edges 564 & 566 and 570 & 572.

The result of the manufacturing steps shown in FIGS. 6A-6I is a balloon endoscope constructed and operative in accordance with a preferred embodiment of the present invention. A particular feature of the present invention in both the retrofit and non-retrofit balloon endoscopes is use of the interior volume of the endoscope for balloon inflation and deflation. It is also a particular feature of the present invention that retrofit of a conventional endoscope as a balloon endoscope requires only modification of the bending section of the endoscope.

It will be appreciated by persons skilled in the art that the present invention is not limited by what has been particularly shown and described herein above. Rather the scope of the present invention includes both combinations and sub-combinations of the various features described hereinabove as well as variations and modifications which would occur to persons skilled in the art upon reading the specifications and which are not in the prior art.

The invention claimed is:

1. A method of manufacture of a balloon endoscope comprising:
   providing an at least partially incomplete endoscope having a selectably pressurizable interior volume;
   providing at least one aperture in an outer sheath of said endoscope, said at least one aperture configured to communicate with said selectably pressurizable interior volume; and
   providing a selectably inflatable balloon over said outer sheath and in sealing engagement therewith, said balloon being arranged to have a balloon volume overlying said at least one aperture; and
   wherein said providing an at least partially incomplete endoscope comprises retrofitting said endoscope to remove at least part of said outer sheath thereof.

2. A method of manufacture of a balloon endoscope according to claim 1 and wherein:
   said providing an at least partially incomplete endoscope comprises providing an endoscope lacking at least part of said outer sheath; and
   said providing at least one aperture comprises:
      forming an aperture in an outer sheath; and
      thereafter mounting said outer sheath on said endoscope.

3. A method of manufacture of a balloon endoscope according to claim 1 comprising associating a fluid flow discriminator with said at least one aperture.

4. A method of manufacture of an endoscope comprising:
   providing an at least partially incomplete endoscope;
   providing at least one aperture in an outer sheath of said endoscope and associating a fluid flow discriminator with said at least one aperture; and
   wherein said providing an at least partially incomplete endoscope comprises retrofitting said endoscope to remove at least part of said outer sheath thereof.

5. A method of manufacture of an endoscope according to claim 4 and also comprising providing a selectably inflatable balloon over said outer sheath and in sealing engagement therewith, said balloon being arranged to have a balloon volume overlying said at least one aperture.

6. A method of manufacture of a balloon endoscope according to claim 4 and wherein:
   said providing an at least partially incomplete endoscope comprises providing an endoscope lacking at least part of said outer sheath; and
   said providing at least one aperture comprises:
      forming an aperture in an outer sheath; and
      thereafter mounting said outer sheath on said endoscope.

7. The method of manufacture of a balloon endoscope according to claim 1, wherein the selectably pressurizable interior volume is confined within a reinforcement mesh.

8. The method of manufacture of a balloon endoscope according to claim 7, wherein the at least one aperture is configured to communicate with the selectably pressurizable interior volume inwardly of the reinforcement mesh.

9. The method of manufacture of claim 1, wherein said retrofitting comprises removing a first bending rubber sheath from said endoscope and wherein said at least one aperture is provided in a second bending rubber sheath.

10. The method of manufacture of claim 9, wherein said at least one aperture is provided in said second bending rubber sheath before mounting said second rubber sheath to said endoscope.

* * * * *

UNITED STATES PATENT AND TRADEMARK OFFICE
CERTIFICATE OF CORRECTION

PATENT NO. : 10,610,086 B2
APPLICATION NO. : 16/048031
DATED : April 7, 2020
INVENTOR(S) : Gad Terliuc et al.

Page 1 of 2

It is certified that error appears in the above-identified patent and that said Letters Patent is hereby corrected as shown below:

On the Title Page

Column 1, Item (72), Line 2, under Inventors, delete "Givataim" and insert --Giv'atayim--.

On Page 2, Column 2, Item (56), Line 65, under U.S. Patent Documents, delete "Fuji Kura" and insert --Fujikura--.

On Page 2, Column 2, Item (56), Line 75, under U.S. Patent Documents, delete "Sekiauchi" and insert --Sekiguchi--.

On Page 3, Column 1, Item (56), Line 14, under Foreign Patent Documents, delete "1/2008" and insert --1/2009--.

On Page 3, Column 2, Item (56), Line 15, under Foreign Patent Documents, delete "4/2007" and insert --3/1987--.

On Page 3, Column 2, Item (56), Line 17, under Foreign Patent Documents, delete "6/2008" and insert --11/2006--.

On Page 3, Column 2, Item (56), Line 57, under Foreign Patent Documents, delete "5/2006" and insert --6/2006--.

On Page 3, Column 2, Item (56), Line 67, under Foreign Patent Documents, delete "10/2007" and insert --11/2007--.

On Page 4, Column 1, Item (56), Line 11, under Other Publications, delete "PCT-IL201 I-000222." and insert --PCT-IL2011-000222.--.

On Page 4, Column 1, Item (56), Lines 13-14, under Other Publications, delete "PCT-IL201 I-000222." and insert --PCT-IL2011-000222.--.

<div style="text-align: right;">
Signed and Sealed this
Fifteenth Day of September, 2020

Andrei Iancu
*Director of the United States Patent and Trademark Office*
</div>

CERTIFICATE OF CORRECTION (continued)
U.S. Pat. No. 10,610,086 B2

On Page 4, Column 1, Item (56), Lines 19-20, under Other Publications, delete "en do scopes- entero scopes" and insert --endoscopes-enteroscopes--.

On Page 4, Column 2, Item (56), Line 7, under Other Publications, delete "TS-13 101" and insert --TS-13101--.

On Page 4, Column 2, Item (56), Line 35, under Other Publications, delete "ST- SB 1" and insert --ST-SB1--.

On Page 4, Column 2, Item (56), Line 36, under Other Publications, delete "sb1 1," and insert --sb1,--.

On Page 4, Column 2, Item (56), Line 38, under Other Publications, delete "SIF-Q 1 80" and insert --SIF-Q180--.

In the Drawings

On Sheet 13 of 26, FIG. 5F, Line 5, delete "POLIP" and insert --POLYP--.

On Sheet 13 of 26, FIG. 5F, Line 8, delete "POLIP" and insert --POLYP--.

On Sheet 13 of 26, FIG. 5F, Line 15, delete "POLIP" and insert --POLYP--.

On Sheet 16 of 26, FIG. 5I, Line 3, delete "WITHRDAW" and insert --WITHDRAW--.

In the Specification

In Column 2, Line 9, delete "11" and insert --II--.

In Column 6, Line 43, delete "the the" and insert --the--.

In Column 7, Line 23, after "with" insert --the--.

In the Claims

In Column 22, Line 22, Claim 6, delete "A method of manufacture of a balloon endoscope" and insert --A method of manufacture of an endoscope--.

In Column 22, Line 39, Claim 9, delete "The method of manufacture" and insert --A method of manufacture of a balloon endoscope--.

In Column 22, Line 43, Claim 10, delete "The method of manufacture" and insert --A method of manufacture of a balloon endoscope--.